(12) United States Patent
Metchik et al.

(10) Patent No.: US 11,026,788 B2
(45) Date of Patent: Jun. 8, 2021

(54) LOADER AND RETRIEVER FOR TRANSCATHETER HEART VALVE, AND METHODS OF CRIMPING TRANSCATHETER HEART VALVE

(71) Applicant: Edwards Lifesciences Corporation, Irvine, CA (US)

(72) Inventors: Asher L. Metchik, Newport Beach, CA (US); Thanh V. Nguyen, Irvine, CA (US); Raz Biran, Karkour (IL); Arvin T. Chang, Yorba Linda, CA (US); Tarannum Nagpurwala, Tustin, CA (US); Jeff Lindstrom, Coto de Caza, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 390 days.

(21) Appl. No.: 15/238,605

(22) Filed: Aug. 16, 2016

(65) Prior Publication Data
US 2017/0049567 A1    Feb. 23, 2017

Related U.S. Application Data

(60) Provisional application No. 62/207,879, filed on Aug. 20, 2015.

(51) Int. Cl.
*A61F 2/24* (2006.01)
*A61F 2/00* (2006.01)
*A61F 2/95* (2013.01)

(52) U.S. Cl.
CPC .......... *A61F 2/2433* (2013.01); *A61F 2/0095* (2013.01); *A61F 2/2436* (2013.01); *A61F 2/9522* (2020.05); *A61F 2250/0039* (2013.01)

(58) Field of Classification Search
CPC .......... A61F 2/2427–2/2439; A61F 2/95–2/97; A61F 2/0095; A61F 2002/9522;
(Continued)

(56) References Cited

U.S. PATENT DOCUMENTS

| 4,035,849 A | 7/1977 | Angell et al. |
| 4,592,340 A | 6/1986 | Boyles |

(Continued)

FOREIGN PATENT DOCUMENTS

| DE | 19532846 A1 | 3/1997 |
| DE | 19907646 A1 | 8/2000 |

(Continued)

OTHER PUBLICATIONS

International Search Report for International Application No. 16837898.2, completed Oct. 29, 2018.

*Primary Examiner* — Kathleen S Holwerda
(74) *Attorney, Agent, or Firm* — Lewis Roca Rothgerber & Christie; Joel B. German

(57) ABSTRACT

A loader and method for loading a transcatheter heart valve into a delivery sheath or catheter is described that is also configured to facilitate retrieval of the heart valve back through the delivery sheath while protecting the delivery sheath from damage. Another loader provides for easier crimping and loading of a THV into a delivery sheath or catheter from a storage jar or container. A method for crimping a THV facilitates easier end user preparation of the valve for implantation and reduces the likelihood of tissue deformation in the valve during storage. These devices and methods for deploying THVs simplify the valve replacement procedure.

20 Claims, 23 Drawing Sheets

(58) Field of Classification Search
CPC ....... A61F 2250/0039; A61M 25/0097; A61M 25/0662; A61M 39/06–0693; A61M 2039/1072; A61M 2039/1077; A61M 2039/1083; A61M 2039/1088; A61M 2039/063; A61M 2039/0626; A61M 2039/0633; A61M 2039/064; A61M 2039/0646; A61M 2039/066; A61M 2039/0653; A61M 2039/0666; A61B 17/3498; Y10S 128/912
See application file for complete search history.

(56) References Cited

U.S. PATENT DOCUMENTS

| | | | |
|---|---|---|---|
| 4,994,077 | A | 2/1991 | Dobben |
| 5,059,177 | A | 10/1991 | Towne et al. |
| 5,059,186 | A * | 10/1991 | Yamamoto ......... A61M 25/0111 600/435 |
| 5,312,355 | A * | 5/1994 | Lee .................. A61M 25/0668 604/160 |
| 5,411,552 | A | 5/1995 | Andersen et al. |
| 5,554,185 | A | 9/1996 | Block et al. |
| 5,591,195 | A | 1/1997 | Taheri et al. |
| 5,599,305 | A | 2/1997 | Hermann et al. |
| 5,613,954 | A * | 3/1997 | Nelson ............... A61B 17/3421 604/167.03 |
| 5,639,274 | A | 6/1997 | Fischell et al. |
| 5,728,068 | A | 3/1998 | Leone et al. |
| 5,840,081 | A | 11/1998 | Andersen et al. |
| 5,911,710 | A * | 6/1999 | Barry ................ A61M 39/0693 604/167.04 |
| 5,968,068 | A | 10/1999 | Dehdashtian et al. |
| 6,168,614 | B1 | 1/2001 | Andersen et al. |
| 6,217,585 | B1 | 4/2001 | Houser et al. |
| 6,379,372 | B1 | 4/2002 | Dehdashtian et al. |
| 6,454,799 | B1 | 9/2002 | Schreck |
| 6,458,153 | B1 | 10/2002 | Bailey et al. |
| 6,461,382 | B1 | 10/2002 | Cao |
| 6,527,979 | B2 | 3/2003 | Constantz et al. |
| 6,582,462 | B1 | 6/2003 | Andersen et al. |
| 6,652,578 | B2 | 11/2003 | Bailey et al. |
| 6,730,118 | B2 | 5/2004 | Spenser et al. |
| 6,733,525 | B2 | 5/2004 | Yang et al. |
| 6,767,362 | B2 | 7/2004 | Schreck |
| 6,830,584 | B1 | 12/2004 | Seguin |
| 6,893,460 | B2 | 5/2005 | Spenser et al. |
| 6,908,481 | B2 | 6/2005 | Cribier |
| 7,018,406 | B2 | 3/2006 | Seguin et al. |
| 7,018,408 | B2 | 3/2006 | Bailey et al. |
| 7,276,084 | B2 | 10/2007 | Yang et al. |
| 7,318,278 | B2 | 1/2008 | Zhang et al. |
| 7,374,571 | B2 | 5/2008 | Pease et al. |
| 7,393,360 | B2 | 7/2008 | Spenser et al. |
| 7,510,575 | B2 | 3/2009 | Spenser et al. |
| 7,585,321 | B2 | 9/2009 | Cribier |
| 7,618,446 | B2 | 11/2009 | Andersen et al. |
| 7,785,366 | B2 | 8/2010 | Maurer et al. |
| 8,029,556 | B2 | 10/2011 | Rowe |
| 8,167,932 | B2 | 5/2012 | Bourang et al. |
| 8,449,606 | B2 | 5/2013 | Eliasen et al. |
| 8,657,789 | B2 | 2/2014 | Guo et al. |
| 2002/0032481 | A1 | 3/2002 | Gabbay |
| 2003/0050694 | A1 | 3/2003 | Yang et al. |
| 2004/0133263 | A1 | 7/2004 | Dusbabek et al. |
| 2004/0186565 | A1 | 9/2004 | Schreck |
| 2004/0260389 | A1 | 12/2004 | Case et al. |
| 2005/0033239 | A1 * | 2/2005 | Argentine ......... A61M 39/0606 604/167.04 |
| 2005/0096736 | A1 | 5/2005 | Osse et al. |
| 2005/0203614 | A1 | 9/2005 | Forster et al. |
| 2005/0203617 | A1 | 9/2005 | Forster et al. |
| 2006/0025857 | A1 | 2/2006 | Bergheim et al. |
| 2007/0005131 | A1 | 1/2007 | Taylor |
| 2007/0203575 | A1 | 8/2007 | Forster et al. |
| 2007/0265700 | A1 | 11/2007 | Eliasen et al. |
| 2008/0125853 | A1 | 5/2008 | Bailey et al. |
| 2008/0294230 | A1 | 11/2008 | Parker |
| 2009/0157175 | A1 | 6/2009 | Benichou |
| 2009/0276040 | A1 | 11/2009 | Rowe et al. |
| 2009/0281619 | A1 | 11/2009 | Le et al. |
| 2009/0319037 | A1 | 12/2009 | Rowe et al. |
| 2010/0049313 | A1 | 2/2010 | Alon et al. |
| 2010/0198347 | A1 | 8/2010 | Zakay et al. |
| 2011/0015729 | A1 | 1/2011 | Jimenez et al. |
| 2011/0046712 | A1 | 2/2011 | Melsheimer et al. |
| 2011/0092910 | A1 * | 4/2011 | Schultz ............. A61B 17/3415 604/165.04 |
| 2011/0208296 | A1 | 8/2011 | Duffy et al. |
| 2011/0301700 | A1 | 12/2011 | Fish et al. |
| 2012/0123529 | A1 | 5/2012 | Levi et al. |
| 2012/0172980 | A1 | 7/2012 | DuMontelle |
| 2013/0317598 | A1 | 11/2013 | Rowe et al. |
| 2015/0190225 | A1 | 7/2015 | Maimon et al. |

FOREIGN PATENT DOCUMENTS

| | | |
|---|---|---|
| EP | 592410 A1 | 4/1994 |
| EP | 850607 A1 | 7/1998 |
| EP | 1796597 A2 | 6/2007 |
| FR | 2815844 A1 | 5/2002 |
| WO | 1991017720 A1 | 11/1991 |
| WO | 1998029057 A1 | 7/1998 |
| WO | 01049213 A2 | 7/2001 |
| WO | 0154625 A1 | 8/2001 |
| WO | 01076510 A2 | 10/2001 |
| WO | 0222054 A1 | 3/2002 |
| WO | 0236048 A1 | 5/2002 |
| WO | 0247575 A2 | 6/2002 |
| WO | 0347468 A1 | 6/2003 |
| WO | 2005084595 A1 | 9/2005 |
| WO | 2005102015 A2 | 11/2005 |
| WO | 2006111391 A1 | 10/2006 |
| WO | 2006138173 A2 | 12/2006 |
| WO | 2007047488 A2 | 4/2007 |
| WO | 200767942 A1 | 6/2007 |
| WO | 2010121076 A2 | 10/2010 |

* cited by examiner

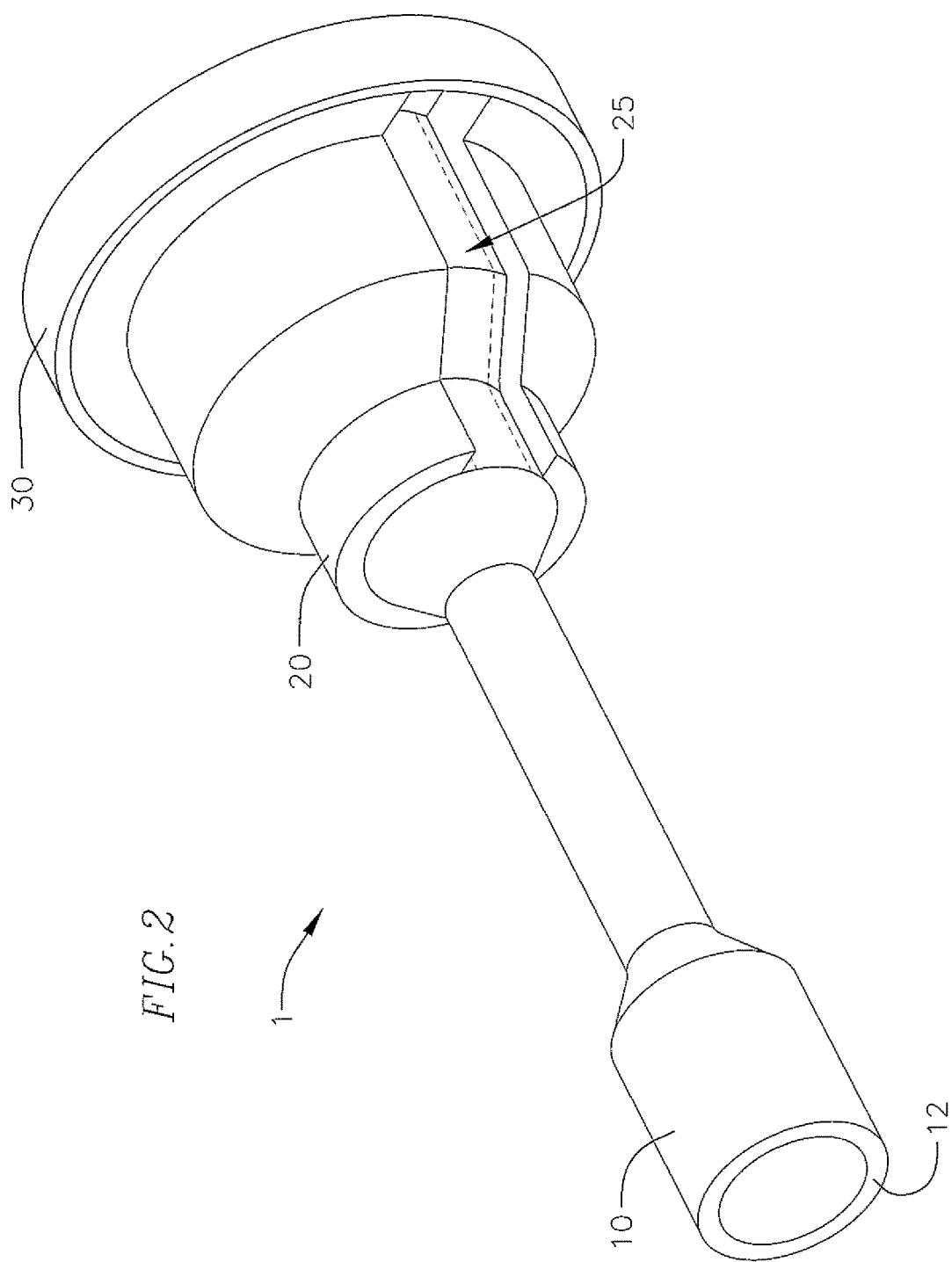

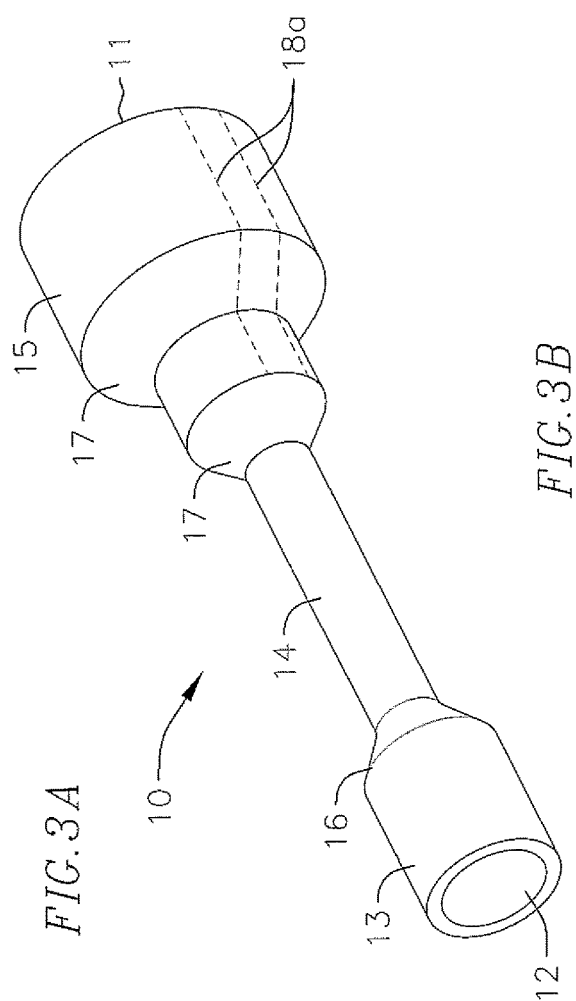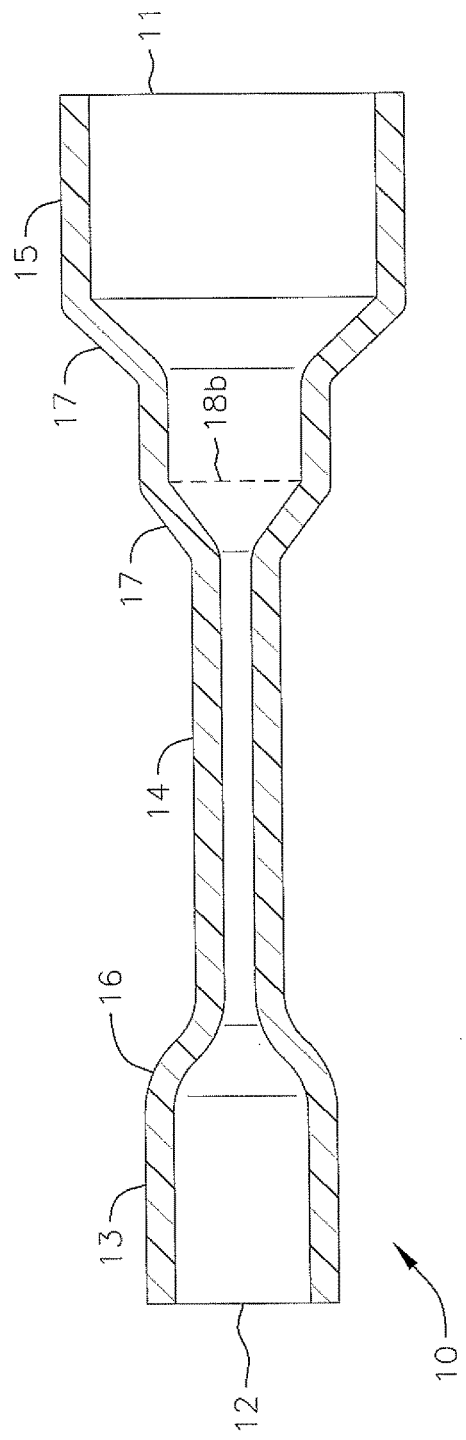

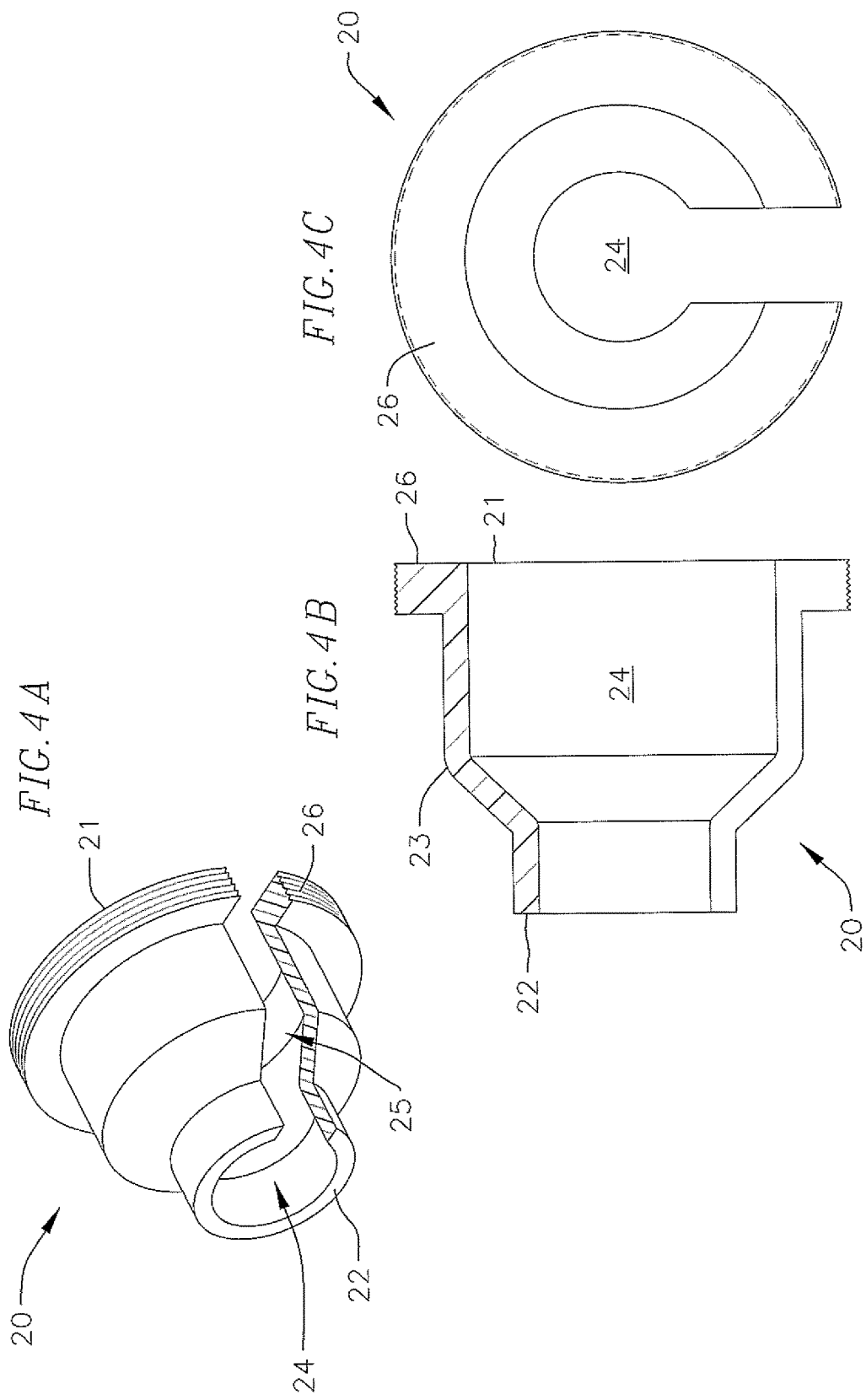

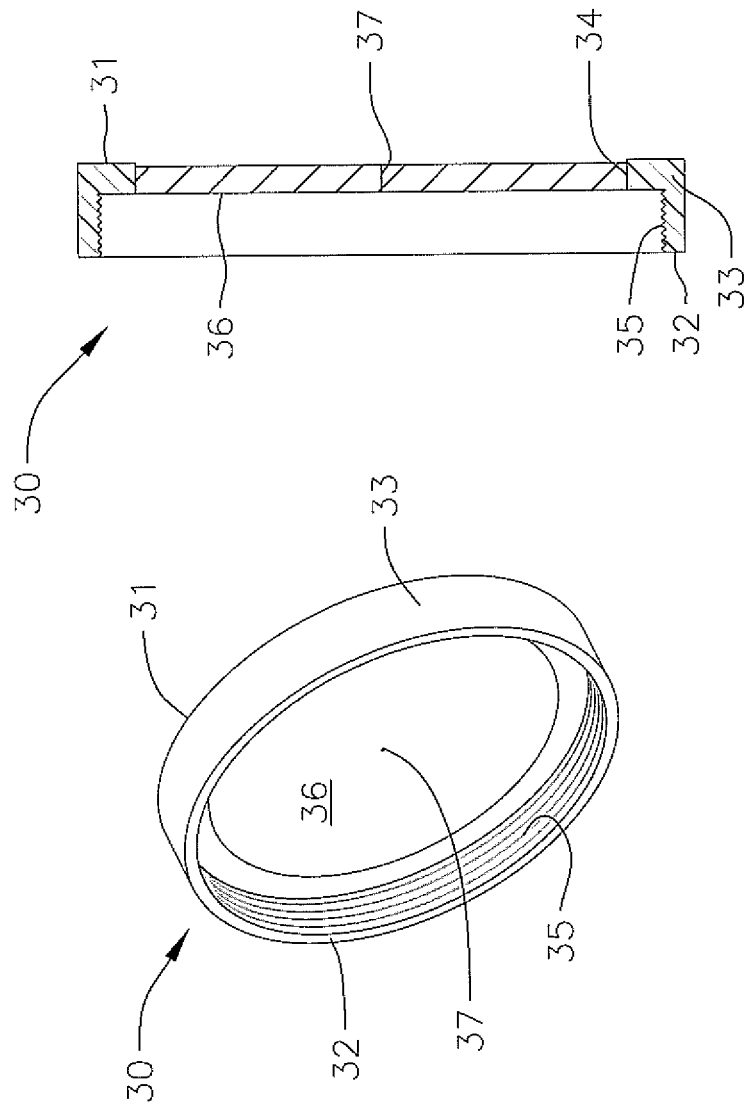

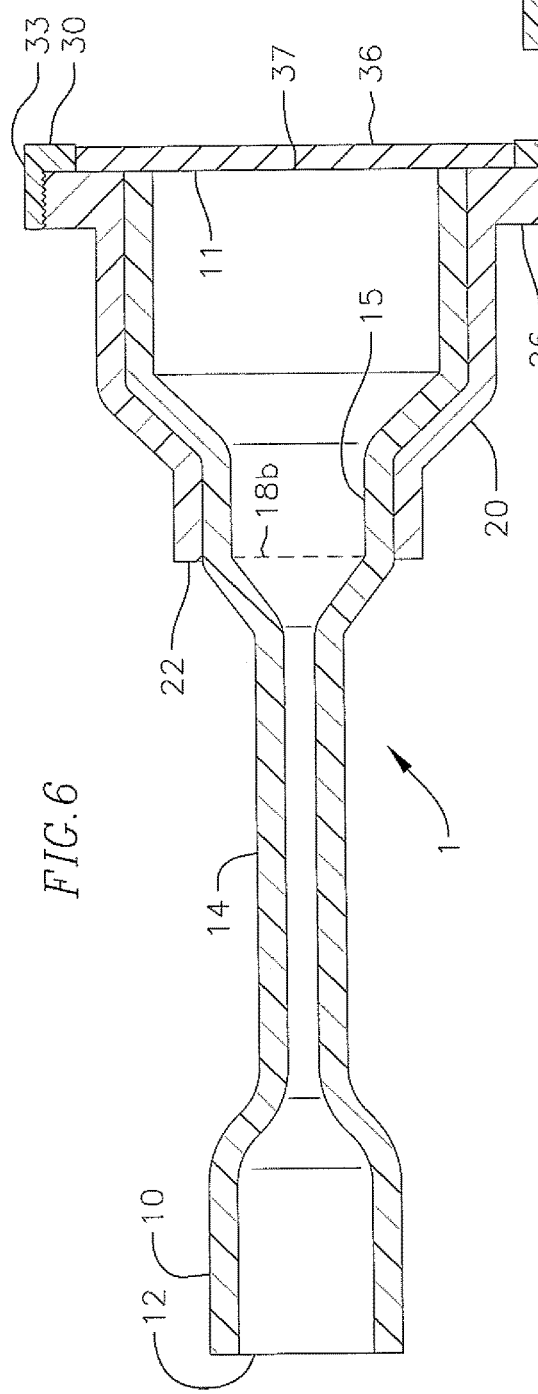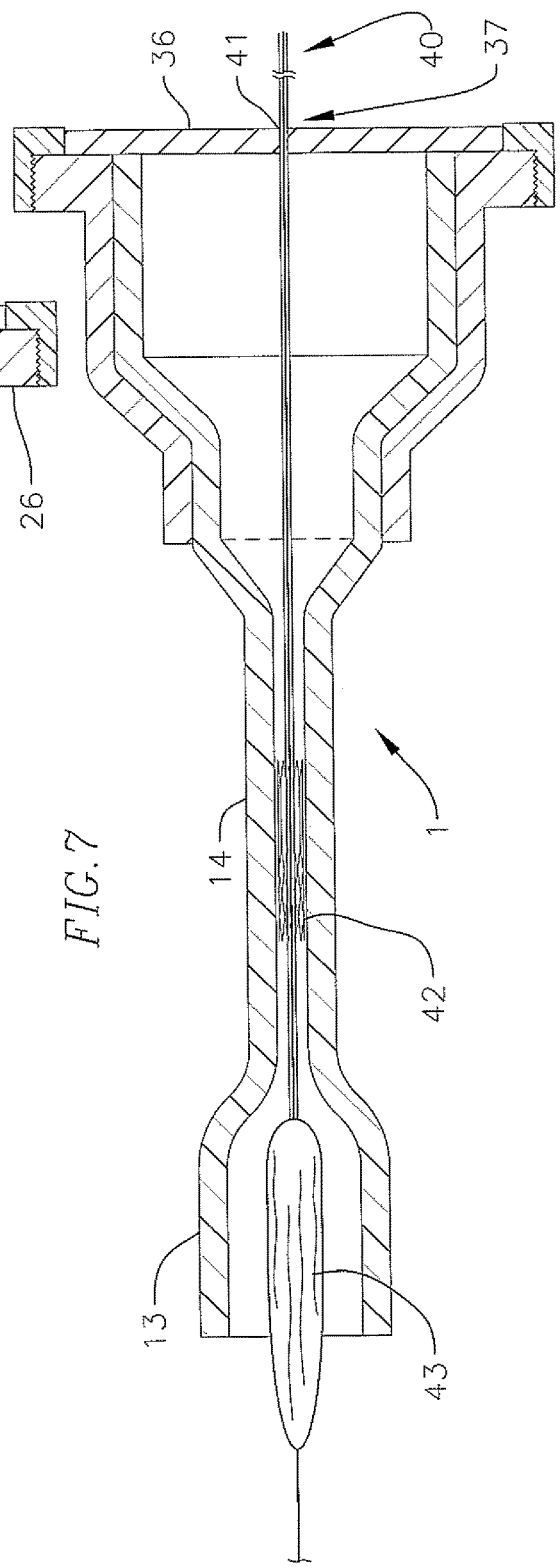

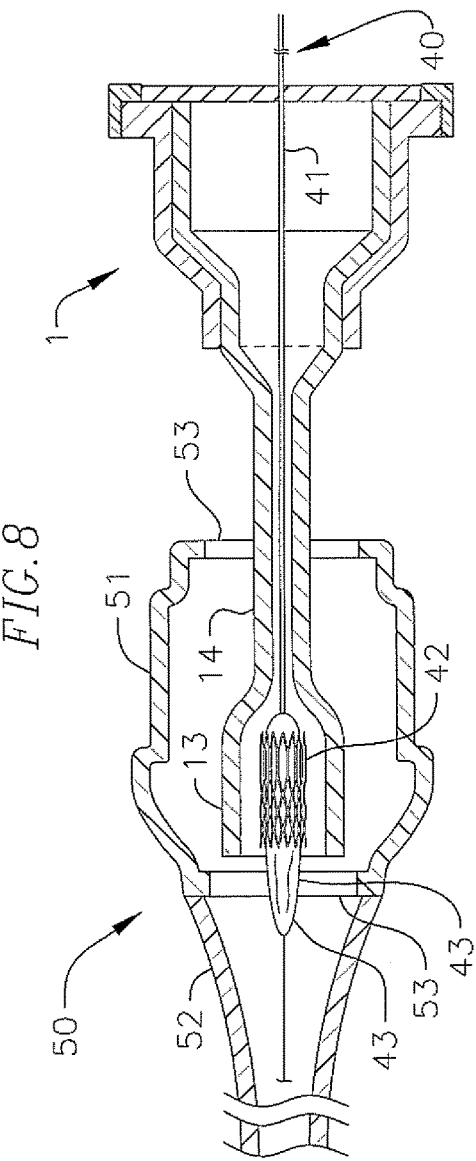
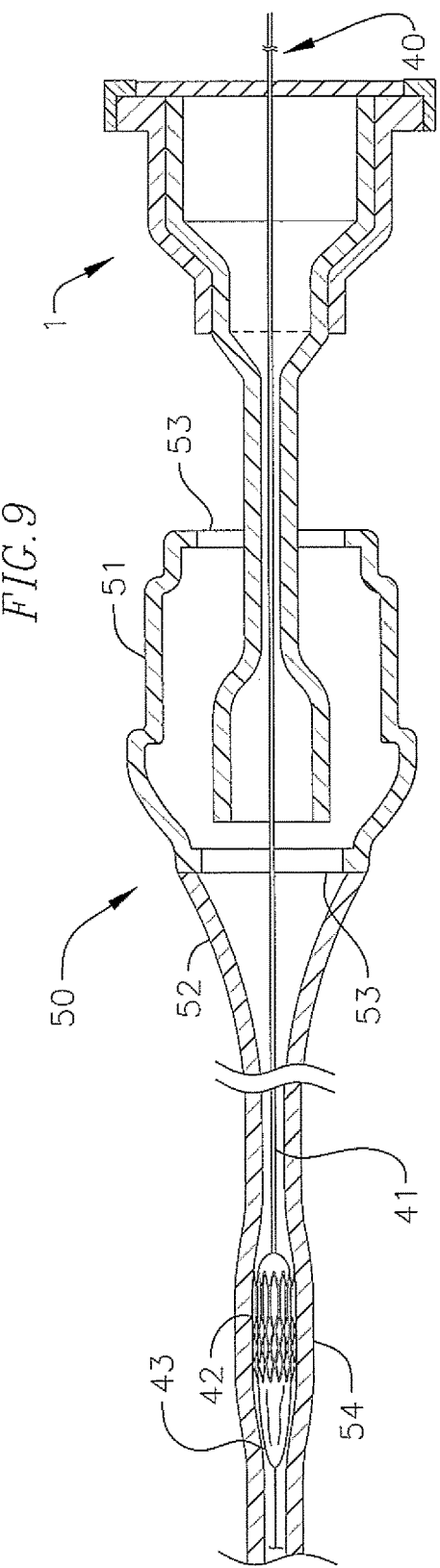

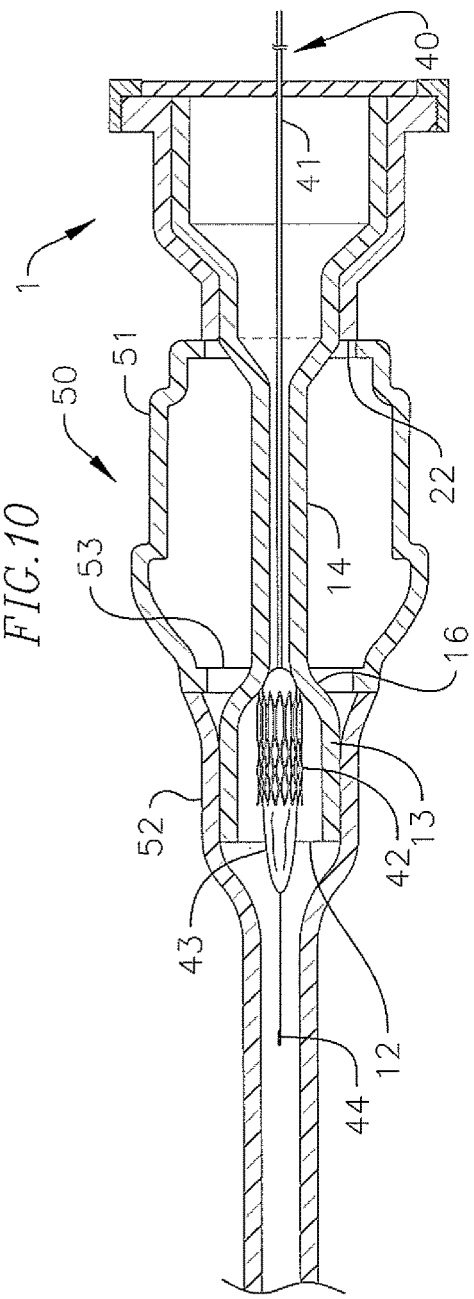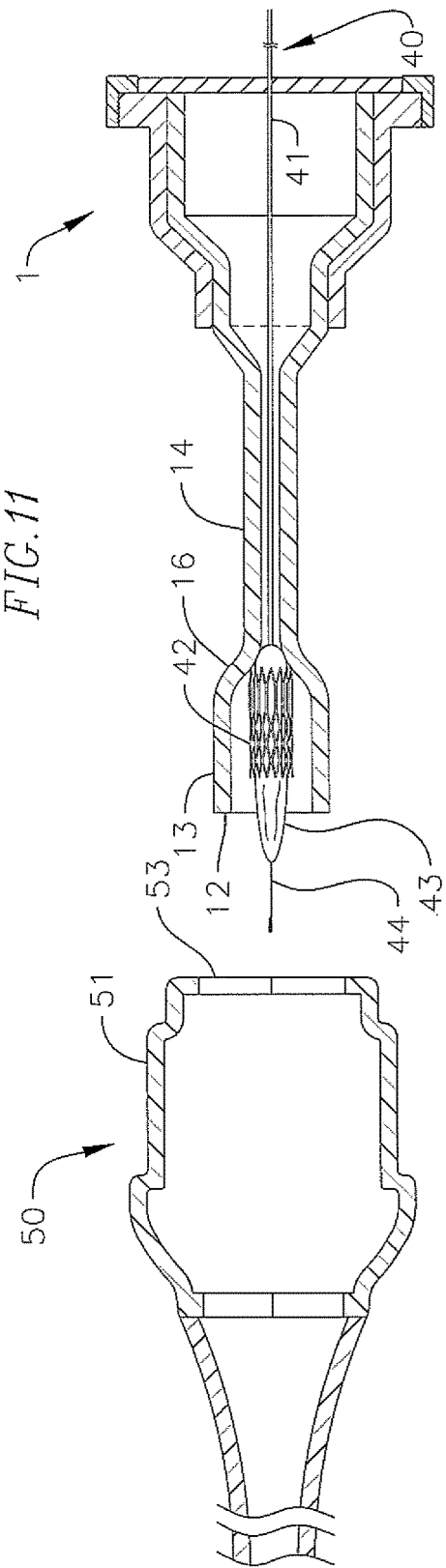

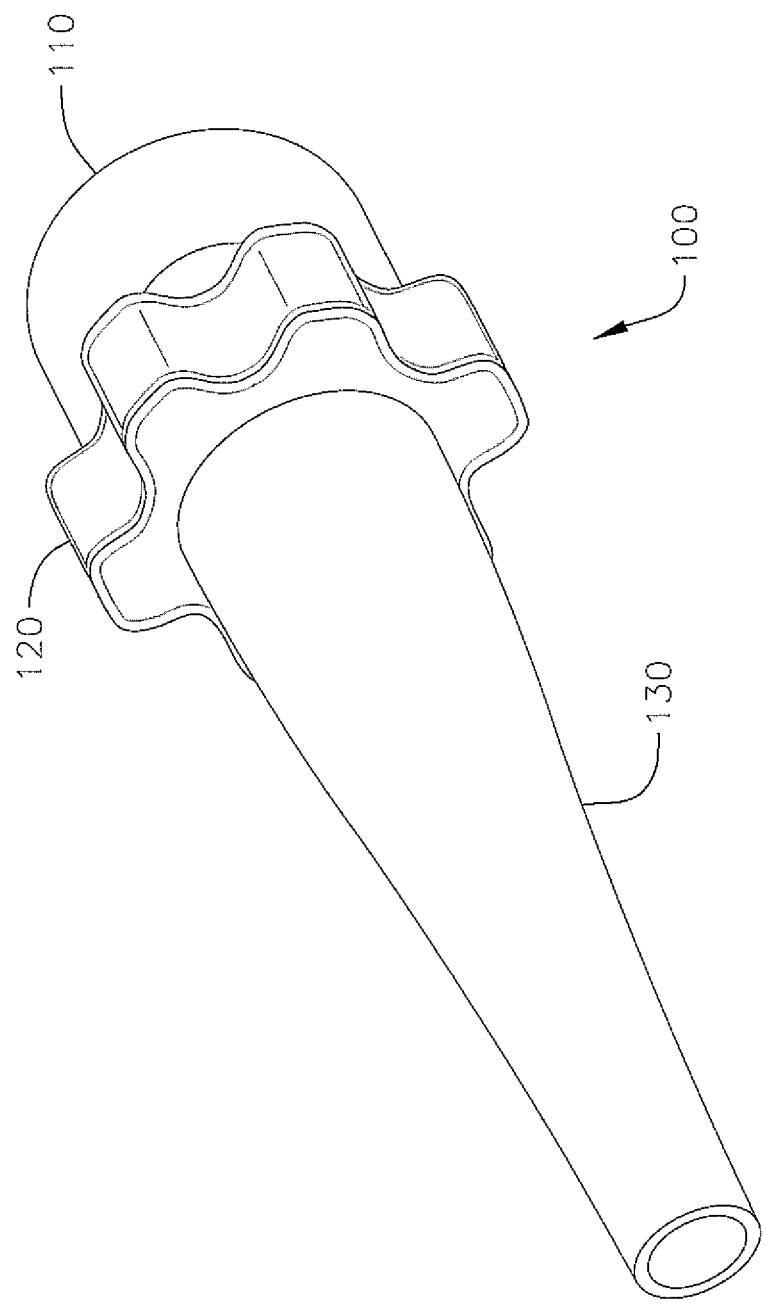

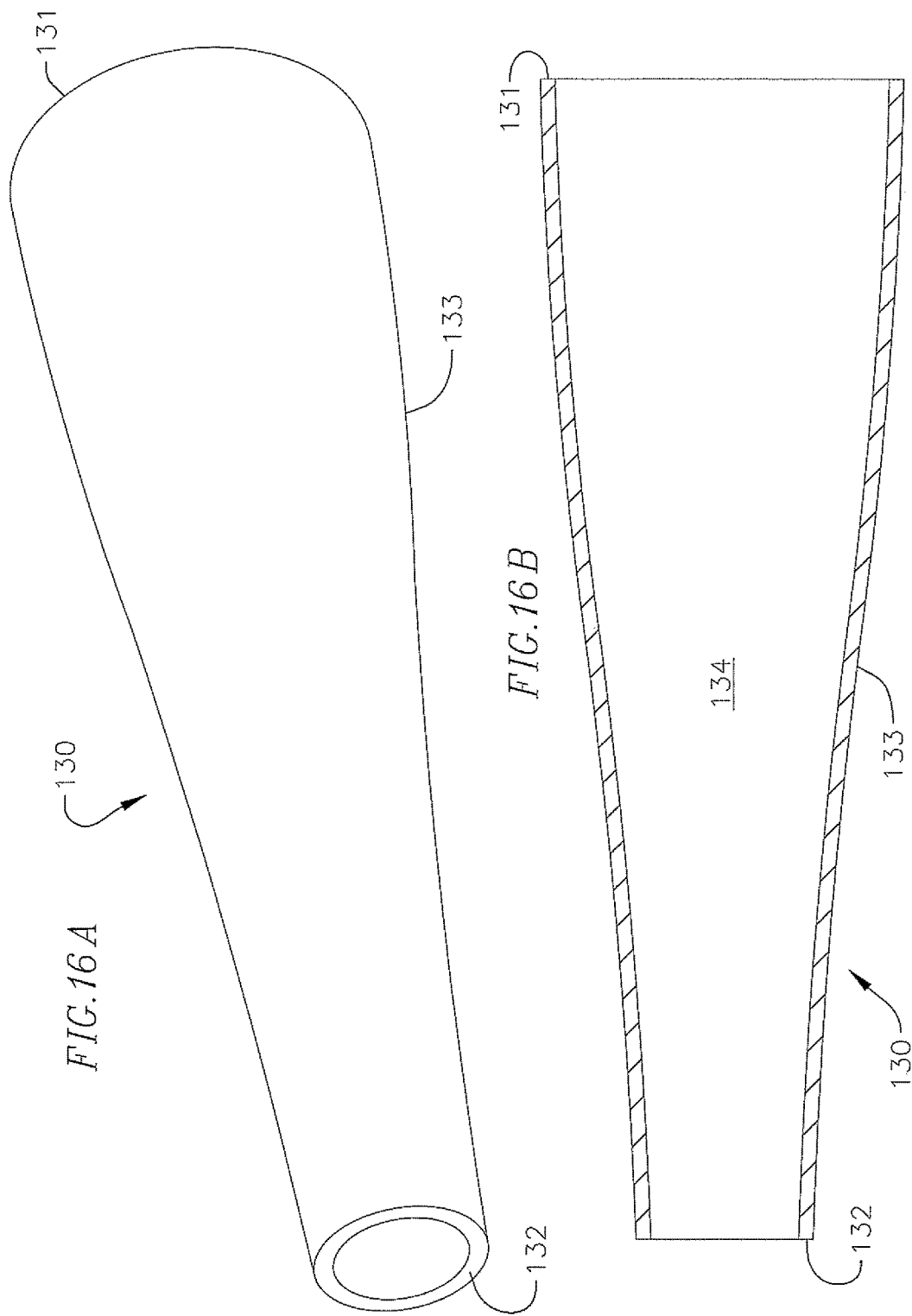

LOADER AND RETRIEVER FOR TRANSCATHETER HEART VALVE, AND METHODS OF CRIMPING TRANSCATHETER HEART VALVE

CROSS-REFERENCE TO RELATED APPLICATION(S)

The present application claims priority to and the benefit of U.S. Provisional Patent Application Ser. No. 62/207,879, filed Aug. 20, 2015, the contents of which are hereby incorporated by reference in their entirety.

BACKGROUND

Field

The invention generally relates to medical devices and procedures associated with transcatheter prosthetic heart valves that are employed to replace diseased heart valves. Embodiments include devices for loading a transcatheter heart valve into a delivery sheath, and for facilitating retrieval of the heart valve through a hub of the delivery sheath. Other embodiments include devices and methods for easier crimping of the valve prior to loading into a delivery sheath.

Description of Related Art

Prosthetic heart valves that can be delivered percutaneously or less invasively, compared to being implanted via open heart surgery, have gained popularity in recent years, and research and development in this area has increased. Prior to this, conventional heart valve surgery involved accessing the heart through a sternotomy or other incision in the chest, while also having to place the patient on cardiopulmonary bypass. Such procedures were very invasive and complicated, and also required lengthy recovery periods for the patients.

Less invasive devices and methods that can be used to deliver prosthetic valves have since been researched and developed. In some instances, a prosthetic valve is delivered to an implant site at the heart endovascularly. For example, in order to deliver a prosthetic aortic valve to the heart, an access site can be made at a patient's groin area to access the femoral artery, and the prosthetic valve can be delivered endovascularly past the aortic bifurcation, up the aorta, and to the aortic valve of the heart for implantation. In these cases, a prosthetic valve is generally collapsed or crimped to reduce its radial width, and is delivered through a catheter and/or a sheath through the various blood vessels, in order to deliver the replacement valve to the heart. Percutaneous or otherwise less invasive heart valve repair or replacement has therefore become possible using such transcatheter heart valves and associated delivery devices and methods in this manner.

As these transcatheter heart valves and other endovascular devices improve and become more commercially available and competitive, more emphasis has been placed on reducing the profile of the replacement valves in their crimped configurations, since reducing the profile of the devices will ease delivery of the devices to the implant sites. However, there has been limited research directed to whether the devices and techniques used to crimp the replacement valves can be realized without damaging the tissue leaflets, or reducing or compromising other functionality of the replacement valves after the valves have been expanded at the implant sites.

Furthermore, as noted above, different catheters and sheaths can be used in transcatheter surgical procedures to aid in delivery of the replacement valves. Sheaths that extend through at least a portion of the blood vessels can protect the vessels from ends, edges, and other features of the implants or delivery devices that could tear, rupture or otherwise damage the blood vessel walls. In recent times, expandable sheaths have been developed, in order to accommodate advancement of larger prostheses and/or delivery systems through the blood vessels. When a prosthetic or part of a delivery system passes through a portion of the expandable sheath, the expandable sheath can expand locally, via for example various mechanical expanding means, and can abut against the blood vessel walls, and in some cases cause the vessel walls to expand as well in a less traumatic manner, in order to accommodate the larger features passing therethrough. As such, development has moved towards using such expandable sheaths as delivery systems for transcatheter heart valves, over traditional stiff tube sheaths.

There has been little research, however, into how to more effectively introduce a prosthetic replacement valve and/or delivery system into the above-described sheath systems. Furthermore, there has been limited research into different devices and/or methods that can be used in conjunction with the existing expandable sheath systems, to further ease or simplify the delivery or implantation process, or to deal with other issues that can arise during valve delivery.

SUMMARY

Features of the invention are directed to a loader tube and assembly for a transcatheter delivery system, where a crimped transcatheter heart valve can be loaded into a delivery sheath, and can be retrieved from the delivery sheath and removed from a patient's body without removing the delivery sheath from the access site. Other features of the invention are directed to an assembly and method for more easily facilitated crimping of a transcatheter heart valve prior to loading the replacement valve into the delivery sheath. Still other features of the invention are directed to devices and methods for more effectively crimping a transcatheter heart valve prior to delivery of the replacement valve in order to reduce shrinkage or other deformation or damage that can occur to the leaflet tissue of the valve, and to improve effectiveness of valve operation or functionality after implantation.

In an embodiment of the invention, a loader assembly for loading a transcatheter heart valve into a delivery sheath for delivering the heart valve into a body of a patient includes a loader tube having a first end, a second end, and a central axis extending through the first and second ends, the loader tube having a tube wall defining a coaxial bore, wherein the tube wall has a first section at the first end with a first diameter, a second section connected to a distal end of the first section and having a second diameter smaller than the first diameter, and a third section connected to a distal end of the second section and having a third diameter greater than the second diameter, and at least one seal configured to maintain hemostasis in the loader tube when the coaxial bore of the loader tube is in communication with a blood vessel of the patient.

According to another embodiment of the invention, a method of using a loader assembly to retrieve a transcatheter heart valve from a body of a patient after the heart valve and a delivery system for the heart valve have been inserted into the body through a delivery sheath that provides access into the body, includes inserting the loader assembly through a hub of the delivery sheath, such that a distal end of the loader assembly extends distally from a hemostatic seal of the hub of the delivery sheath, wherein the delivery system extends through the delivery sheath and the loader assembly, moving the heart valve and a balloon of the delivery system on which the heart valve is positioned towards the loader assembly, moving the heart valve and the balloon into a distal section of the loader assembly, wherein a width of an opening at the distal end of the loader assembly is greater than a width of the heart valve and an axial length of the distal section of the loader assembly is greater than a length of the heart valve when the heart valve is retrieved, and removing the loader assembly from a proximal end of the delivery sheath while the heart valve and the balloon are positioned in the distal section of the loader assembly.

According to yet another embodiment of the invention, a loader assembly for loading a transcatheter heart valve into a delivery sheath for delivering the heart valve into a body of a patient includes a storage container configured to store the heart valve, a crimping apparatus having a first end connectable to the storage container and a second end, the crimping apparatus being configured to crimp the heart valve from a first expanded configuration to a second crimped position, and a loader tube connectable to the second end of the crimping apparatus and configured to advance the heart valve into the delivery sheath when the heart valve is in the second crimped position.

According to still another embodiment of the invention, a method of crimping a transcatheter heart valve having a first end and a second end and including a valve frame and a plurality of valve leaflets, includes crimping the heart valve to a first position where the first end of the heart valve is crimped from a first width to a second width smaller than the first width, while the second end of the heart valve remains at the first width, and packaging the heart valve when the heart valve is in the first position.

According to embodiments of the invention, transcatheter heart valves can more easily and effectively be introduced into an existing delivery sheath system, where the replacement valve can further be retrieved from the delivery sheath system in a more efficient manner. Furthermore, embodiments of the invention can simplify the valve introduction process for a practitioner or other end user, and can also improve operation of the valve once it has been implanted in a patient. According to other embodiments, transcatheter heart valves can be stored in a more effective and efficient manner, to reduce deformation or other damage to the heart valves and to simplify end user requirements.

BRIEF DESCRIPTION OF THE DRAWINGS

Further features and advantages of the invention will become apparent from the description of embodiments using the accompanying drawings. In the drawings:

FIG. 2 shows the loader assembly of FIG. 1 in an assembled state;

FIGS. 3A and 3B show a perspective view and a cross-sectional view, respectively, of a loader tube of the loader assembly according to the first embodiment;

FIGS. 4A-4C show a perspective view, a cross-sectional view, and a top view, respectively, of a hub of the loader assembly according to the first embodiment;

FIGS. 5A and 5B show a perspective view and a cross-sectional view, respectively, of a cap of a loader assembly according to the first embodiment;

FIG. 6 shows a cross-sectional view of the loader assembly according to the first embodiment;

FIGS. 7-9 show steps of inserting a transcatheter heart valve and a delivery system into the loader assembly, and of interfacing the loader assembly with a hub of a delivery sheath, according to the first embodiment;

FIGS. 10 and 11 show steps of retrieving a transcatheter heart valve through the delivery sheath using the loader assembly, according to the first embodiment;

FIG. 13 shows the loader assembly of FIG. 12 in an assembled state;

FIGS. 16A and 16B show a perspective view and a cross-sectional view, respectively, of a loader tube of the loader assembly, according to the second embodiment;

DETAILED DESCRIPTION

Disclosed herein are loading assemblies, arrangements, and methods for use with prosthetic heart valves that allow for simplified and improved delivery of the prosthetic valves into delivery sheath devices or other catheter-based access devices, to facilitate endovascular delivery of the prosthetic valves to the heart of a patient.

Some transcatheter heart valves (THV), for example, the Edwards Lifesciences SAPIEN™ valve, are designed to be radially crimped to facilitate endovascular delivery to an implant site at a patient's heart. Once positioned at a native valve annulus, the replacement valve is expanded to an operational state, for example, by an expansion balloon provided in the delivery system. The replacement valve can be crimped off of the balloon, and can be aligned onto the balloon once inside the delivery sheath or after the replacement valve and the balloon have exited a distal end of the delivery sheath. During alignment of the crimped replacement valve onto the balloon, the replacement valve can expand somewhat in order to fit the balloon therethrough.

During some procedures, it may become desirable or necessary to retrieve the replacement valve after the valve has already been radially expanded to accommodate the balloon. Some delivery sheaths have been designed so that the slightly expanded valve and balloon assembly can be retracted back into the distal end of the sheath. However, once the replacement valve is in this slightly expanded state, the valve cannot be completely removed from the delivery sheath and the patient's body, because the larger outer diameter of the slightly expanded valve can get caught on the hemostatic seals in the delivery sheath, potentially damaging the seals and causing a hemostatic leak through the sheath. Under these previous constraints, the physician was therefore required to remove the entire delivery sheath in order to remove the valve.

According to various embodiments of the invention, a loading assembly is utilized for loading the prosthetic heart valve through a pre-positioned delivery sheath or catheter at an access site on a patient. The same loading assembly can also later be used to retrieve the replacement valve after the valve has been positioned on a balloon and has been slightly expanded, where the valve and the loading assembly can be removed from the delivery sheath without also having to remove the sheath from the access site on the patient. This will help the physician avoid having to reinsert a delivery sheath or catheter when valve removal is desired.

Figure 1:
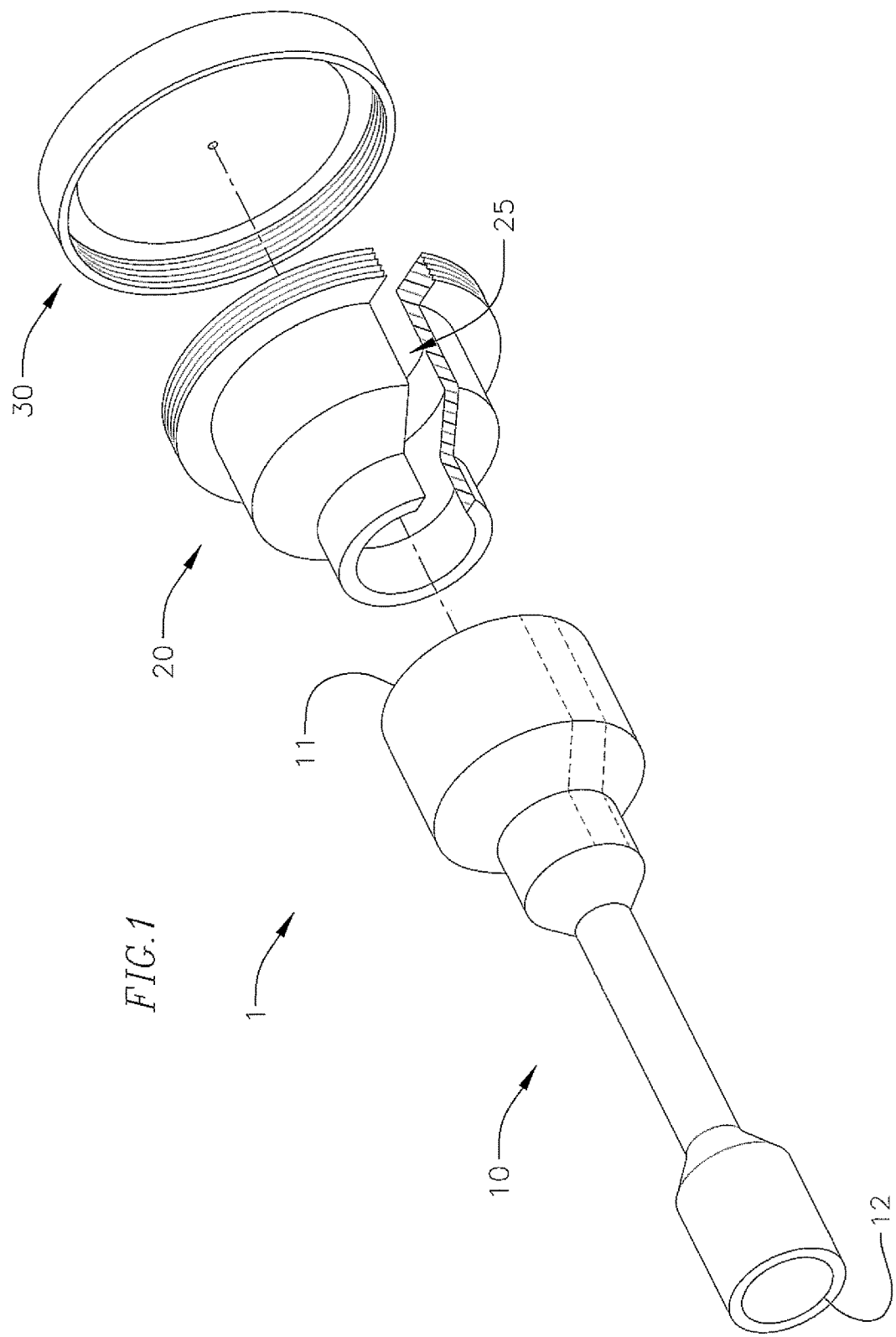
FIG. 1 shows an exploded perspective view of a loader assembly for loading a transcatheter heart valve into a delivery sheath, according to a first embodiment of the invention.

A loader assembly according to an embodiment of the invention is illustrated in FIGS. 1 and 2. The loader assembly 1 is a generally tubular structure that includes a loader tube 10, a hub 20, and a cap 30. The loader tube 10 has a first proximal end 11 with an opening for inserting a prosthetic valve in a crimped state, and a second distal end 12 with an opening through which the crimped prosthetic valve is advanced into a delivery sheath. The hub 20 is attached to the proximal end 11 of the loader tube 10, and includes a slot 25 that runs longitudinally along a wall of the hub 20, which in some embodiments can be used to facilitate attachment of the hub 20 around the loader tube 10. In addition, the cap 30 is attachable to the hub 20, for example, by a threaded engagement. The cap 30 and/or other portions of the loader assembly 1 can form a hemostatic seal to prevent leakage through the loader assembly 1 when the loader assembly is inserted into a delivery sheath at an access site of a patient.

Referring now to FIGS. 3A and 3B, the loader tube 10 includes a tube wall that defines a bore with varying inner diameters extending from the proximal end 11 to the distal end 12. At the proximal end 11, the loader tube 10 has a tube section 15 with an enlarged opening at the proximal end 11 and at least one portion 17 that reduces in diameter towards the distal end 12, to facilitate guiding and inserting of the delivery system and/or crimped valve through the loader tube. In the embodiment shown, the tube section 15 has two such tapering sections 17 that reduce in diameter. In a middle portion of the loader tube 10, a middle tube section 14 has a reduced inner diameter relative to other portions of the loader tube 10. An inner diameter of the tube section 14 is equal to or slightly larger than an outer diameter of a crimped replacement valve that has been crimped off of an expansion balloon, which in some embodiments is the smallest crimped configuration of the valve prosthesis. In this manner, the crimped valve can be temporarily held in the middle tube section 14 of the loader tube 10 by for example, friction or interference forces against an inner wall of the tube section 14, and the crimped valve is restricted from migrating out of tube section 14 absent an additional axial force applied to either the loader assembly 1 or the valve. Distal to the tube section 14 is an enlarged or flared tube section 13 with an enlarged wide-mouth opening at the distal end 12. In the embodiment shown, the opening at the distal end 12 is slightly smaller than the opening at the proximal end 11. The flared distal section 13 is sized to retrieve and hold a crimped valve that has slightly expanded radial width than its original crimped diameter due, for example, to the valve being aligned onto a balloon. An axial length of the tube section 13 is equal to or greater than an axial length of a valve prosthesis when the valve prosthesis is crimped, so that the valve prosthesis can fit fully in the tube section 13 during valve retrieval.

The different diameters between the distal tube section 13 and the middle tube section 14 forms a tapering portion 16 which serves as a hard stop for a slightly expanded valve that is being retrieved back into the loader assembly 1 through the opening at the distal end 12. The tapering portion 16 prevents the retrieved valve from slipping out of the proximal end 11 of the loader and potentially breaking any hemostatic seals before the loader and valve have been fully removed from the rest of the delivery system.

Additionally, the loader tube 10 can further include one or more trails of etched score marks 18a, 18b in the wall of the loader tube 10. In the embodiment shown, two substantially parallel longitudinal lines of score marks 18a extend from the proximal end 11 of the loader tube 10, across the tube section 15, to a transition region between the tube section 15 and the tube section 14. An additional trail of score marks 18b extends circumferentially around the loader tube 10 approximate the region where the score marks 18a end. In addition, the position of the score mark 18b corresponds to a region of the loader tube 10 where the hub 20 ends when the hub 20 is attached to or bonded to the loader tube 10. Additional features and usage of the score marks 18a, 18b will be discussed in greater detail below with relation to operation of the loader assembly 1.

Referring to FIGS. 4A to 4C, the hub 20 has a first proximal end 21 and a second distal end 22. An axial length of the hub 20 corresponds substantially to an axial length of the proximal tube section 15 of the loader tube 10, and a shape of a circumferential wall 23 of the hub 20 corresponds substantially to the shape of the tube section 15, including one of the tapering sections 17 in the illustrated embodiment. The wall 23 of the hub 20 defines a coaxial bore 24 that extends through a center of the hub 20. In addition, a slot 25 runs longitudinally down one side of the hub 20. A circumferential width of the slot 25 is the same as or slightly larger than a distance between the two parallel lines of score marks 18a, so that the score marks 18a are accessible through the slot 25 when the loader tube 10 and the hub 20 are bonded or otherwise assembled together. The hub 20 further has an annular lip 26 adjacent to the proximal end 21 that has a larger diameter than other portions of the hub 20. In the embodiment shown, an outer circumferential surface of the annular lip 26 is threaded or otherwise modified to facilitate engagement with the cap 30.

The cap 30 is illustrated in FIGS. 5A and 5B, and also has a first proximal end 31 and a second distal end 32. The cap 30 includes a frame 33 in the form of an annular ring. The frame 33 has a first portion 34 adjacent to the proximal end 31 with a substantially cylindrical inner surface, and a second portion 35 adjacent to the distal end 32 with a threaded inner surface. The threaded inner surface of the second portion 35 of the cap 30 is configured to interact with the threaded outer surface of the annular lip 26 of the hub 20 to attach the cap 30 to the hub 20. Meanwhile, a seal 36 is attached to the first portion 34 of the frame 33. The seal 36 is attached to the first portion 34 of the frame 33 in one of various manners, for example, via an adhesive or other bonding means. Furthermore, the seal 36 can contribute to forming a hemostatic seal of the loader assembly 1. The seal 36 includes a centrally located expandable opening 37 through which a crimped valve and delivery system can pass, as will be discussed in greater detail below.

FIG. 6 shows a cross-sectional view of an assembled loader assembly 1 according to the first embodiment. As can be seen in FIG. 6, the hub 20 is bonded or otherwise attached to the proximal section 15 of the loader tube 10, where the inner wall of the hub 20 substantially corresponds to the outer wall of the proximal section 15 of the loader tube 10. The distal end 22 of the hub 20 is axially aligned with the circumferential trail of score marks 18b extending around the loader tube 10. Additionally, as can best be seen in FIG. 2, the slot 25 of the hub 20 is aligned with the two lines of score marks 18a, so that the score marks 18a are exposed to the outside of the loader assembly 1 through the slot 25. Additionally, the cap 30 is attached to the proximal end 21 of the hub 20. As indicated above, the cap 30 includes a seal 36, which can facilitate hemostasis through loader assembly 1 during a surgical or other medical procedure. Other seals (not shown) can also be arranged through the loader tube 10, the hub 20, or the cap 30, as needed, for maintaining hemostasis.

Operation of the loader assembly will now be discussed, with reference to FIGS. 7-11. FIGS. 7-9 show steps of inserting a THV and a delivery system into the loader assembly, and of interfacing the loader assembly with a hub of a delivery sheath. In FIG. 7, a valve prosthesis delivery system 40 includes a delivery catheter 41 for supporting and advancing a transcatheter heart valve 42 and an expansion balloon 43 to an implant site. The delivery catheter 41 is generally tubular and has a distal end from which the valve prosthesis 42 and the balloon 43 extend. Furthermore, a guide wire 44 extends through the delivery catheter 41, the valve prosthesis 42, and the balloon 43. The prosthetic valve 42 is crimped around the delivery system 40, and for example, a proximal end of the prosthesis 42 can abut against an end of a feature or advancing tool of the delivery system 40 (not shown). The expandable balloon 43 is positioned distal to the crimped valve prosthesis 42 on the delivery catheter. The valve prosthesis 42 in this embodiment is crimped off of the balloon 43.

The guide wire 44, the uninflated balloon 43, and the crimped valve 42 are inserted through the loader assembly 1. The various features of the delivery system 40 are first inserted through the opening 37 of the cap 30, and then advanced through the middle tube section 14 of the loader tube 10. The balloon 43 can be collapsed and advanced past the middle section 14, while the crimped valve 42 can be positioned in the middle section 14, where, as discussed above, the crimped valve 42 can be temporarily held.

In FIG. 8, the loader assembly 1 holding the delivery system 40 and the crimped valve 42 is inserted into a proximal hub 51 of a delivery sheath device 50. The delivery sheath device 50 can be an expandable sheath system, which includes the hub 51 and an expandable sheath 52 attached to a distal end of the hub 51. The delivery sheath device 50 can also include one or more seals 53 to help maintain hemostasis when the sheath is positioned at an access site in a patient's body. The loader assembly 1 can be configured for use in conjunction with any similar delivery sheath device, and as such, specific details of the sheath device 50 that are not associated with interactions with the loader assembly 1 have been omitted for ease of description.

In one embodiment, the distal end 12 of the loader tube 10 is first inserted into the hub 51 while the delivery system 40 is arranged in the loader assembly 1 as previously described and illustrated with respect to FIG. 7. Alternatively, in the embodiment shown in FIG. 8, the crimped valve 42 can first be advanced past the middle tube section 14 of the loader tube 10 into the enlarged tube section 13 and can be positioned on the balloon 43, while also slightly expanding to accommodate the balloon 43. In this manner, the valve 42 and balloon 43 assembly can be positioned and held in the distal tube section 13 when the loader assembly 1 is inserted into the hub 51 of the sheath device 50.

As can be seen in FIG. 8, when the distal end 12 of the loader tube 10 is approximate the distal end of the hub 51, the relative lengths of the loader assembly 1 and the sheath hub 51 are such that the middle tube section 14 extends out of the proximal end of the hub 51. In this manner, the loader assembly 1 can be advanced further distally relative to the sheath device 50 when retrieval of a valve prosthesis 42 is desired, until the enlarged proximal section 15 of the loader tube 10 or the hub 20 of the loader assembly 1 abuts against a proximal end of the hub 51. This allows the enlarged distal section 13 of the loader tube 10 to extend out of the distal end of the hub 51, and/or any hemostatic seals 53 positioned between the hub 51 and the sheath 52, and into the sheath 52. This configuration will be discussed in greater detail below with respect to FIGS. 10 and 11, directed to retrieval of the valve prosthesis 42.

After the loader assembly 1 is inserted into the hub 51, the loader assembly 1 can be held at the position shown in FIG. 8, where the distal end 12 of the loader tube 10 remains in the hub 51 of the sheath device 50. Meanwhile, the crimped valve prosthesis 42, as well as the delivery system 40 including the catheter 41, the balloon 43, and the guide wire 44, can be aligned with the sheath 52 of the sheath device 50, and then advanced through the distal end of the hub 51 and into the sheath 52. FIG. 9 illustrates an example of a valve prosthesis 42 positioned on balloon 43 being advanced towards the implant site. As can be seen, sheath 52 is expandable, and a portion 54 of the sheath 52 is expanded locally around the prosthesis 42 and balloon 43 assembly, for accommodating the assembly when it passes through the sheath 52. Meanwhile, the loader assembly 1 can be held together with the hub 51 in the position shown in FIGS. 8 and 9 during the rest of the implantation procedure, or can be pulled proximally out of the proximal end of the hub 51, and held apart from the sheath device 50 during the rest of the procedure. It shall be noted that in either of these cases, the delivery catheter 41 of the delivery system 40 still passes through both the loader assembly 1 and the hub 51.

The crimped THV 42 can then be advanced and positioned at the implant site, and can be expanded by the balloon 43 for final implantation. The sheath 52 will only extend to a portion proximal to the implant site (e.g., to a location in the patient's aorta), while the delivery system 40 holding the valve prosthesis 42 exits a distal end of the sheath 52 and advances to the implant site. After the prosthetic valve 42 is positioned and expanded at the implant site, the delivery system 40 can be retrieved through the sheath 52, and the delivery system 40 and the delivery sheath device 50 can both be removed from the access site on the patient.

In some situations, retrieval of the valve prosthesis 42 may become desirable or necessary. For example, during implantation, the valve 42 or part of the delivery system 40 can become damaged, the valve 42 may not expand correctly, or other errors or malfunctions can occur where the physician deems it necessary to completely remove the valve 42 from the patient. Under such circumstances, the loader assembly 1 can be used to facilitate retrieval of the valve 42, where the loader assembly 1, the valve 42, and the delivery system 40 can be removed from the patient, while the delivery sheath device 50 remains in the body. In this manner, reinsertion or repositioning of the sheath device 50 at the patient's access site is not needed, and a new delivery system 40 and/or valve 42 can be delivered through the sheath device 50 more quickly and easily. Previously, absent use of the loader assembly 1, removal of the entire sheath device 50 would be necessary to remove a partially expanded valve 42, since the valve 42 can damage the sheath 52 or one or more hemostatic seals 53 during the retrieval process.

FIGS. 10 and 11 show steps of retrieving a THV 42 through the delivery sheath device 50 using the loader assembly 1. In FIG. 10, the delivery system 40, including the catheter 41 and the balloon 43, along with the partially expanded valve 42 positioned on the balloon 43, have already been retrieved partially through the sheath 52, but have not yet been pulled back into the hub 51. Meanwhile, the loader assembly 1 has been advanced further distally into the hub 51. In cases where the loader assembly 1 was pulled proximally out of the hub 51 after the valve 42 was advanced into the sheath 52, the loader assembly 1 can be inserted back into the sheath device 50 and advanced to the position illustrated in FIG. 10 prior to the valve 42 being pulled back into the hub 51. In the configuration of FIG. 10, the loader assembly 1 has been advanced distally through the hub 51, so that the enlarged tube section 13 protrudes out of the hub 51 and into the sheath 52, where the opening at the distal end 12 of the loader tube 10 has crossed and is distal to one or more hemostatic seals 53 positioned in and/or around the hub 51. A length of the loader assembly 1 relative to the hub 51 allows for the distal end 12 of the loader tube to protrude into the sheath 52 before the enlarged proximal portions of the loader assembly 1 abut against the proximal end of the hub 51.

In the configuration shown in FIG. 10, the balloon 43 and the valve prosthesis 42 that is partially expanded thereon can be pulled back into the enlarged tube section 13 prior to contacting the hub 51 and any seals 53 associated therewith. The valve 42 and balloon 43 are held in the enlarged tube section 13, and the tapered section 16 acts as a hard stop against pulling the partially expanded valve 42 or the balloon 43 any further proximally through the loader tube 10. Therefore, a situation where the physician accidentally removes the valve 42 and the rest of the delivery system 40 through the loader assembly 1 before the loader assembly is removed from the sheath device 50, and potentially damaging the seal 36 of the loader assembly 1, or any other seals in the loader assembly 1 or the sheath device 50, is prevented.

Additionally, since an axial length of the enlarged tube section 13 is equal to or greater than an axial length of the crimped valve prosthesis 42, when the valve 42 is held in the tube section 13, the tube section 13 completely surrounds the valve 42 and protects the sheath device 50, and specifically the seals 53 and other portions of the hub 51, from being damaged by the valve 42 and/or other portions of the delivery device 40.

As shown in FIG. 11, an entire system, including the loader assembly 1, the delivery system 40, and the partially expanded valve 42, can then be safely pulled out from the proximal end of the hub 51 of the delivery sheath device 50. The enlarged tube section 13 protects the seal or seals 53 of the hub 51 from being damaged by the partially expanded valve 42 or the delivery system 40, and the tapered section 16 of the loader tube 10 keeps the valve 42 and balloon 43 in place in the tube section 13, thereby also keeping the seal 36 of the loader assembly 1 from being damaged as well. In this manner, hemostasis can be maintained during removal of the valve 42 from the patient's body, and loss of blood through either the loader assembly 1 or the sheath device 50 can be effectively prevented or minimized.

Since the sheath device 50 remains in place in the patient's body during valve removal, a quicker turnaround can be made to prepare and advance a new delivery system 40 and/or valve 42 assembly through the sheath device 50 for implantation of the valve 42 in the patient.

As discussed above, the loader assembly 1 further includes one or more trails of etched score marks 18a, 18b on the loader tube. The score marks 18a, 18b remain exposed to the outside of the loader assembly 1 after the hub 20 is attached to the loader tube 10. In some circumstances, for example, when it is apparent that there will be no need to retrieve the valve 42 during a procedure, and where the physician requires or would be more comfortable having some additional working length at the proximal side of the hub 51 of the sheath device 50, the large tube section 15, the hub 20, and the cap 30 of the loader assembly 1 can be removed from around the catheter 41 of the delivery system 40. The physician can start at the proximal end 11 of the loader tube 10 and begin peeling away the portion of the loader tube 10 defined by the parallel trails of score marks 18a running inside the slot 25 of the hub 20, until the circumferential score marks 18b are reached. The physician can then peel off the proximal portion of the loader assembly 1 along the score marks 18b, and remove the proximal tube section 15, the hub 20, and the cap 30.

After the proximal portion of the loader assembly 1 has been removed from around the delivery system 40, the distal portion of the loader tube 10, including the middle section 14 and the distal section 13, for example, can be advanced distally completely into the hub 51, so that the seal 53 at the proximal end of the hub 51 helps maintain hemostasis in the system. In other embodiments, additional longitudinal score marks can be etched into the middle section 14 and distal section 13 of the loader tube 10, so that complete removal of the loader assembly 1 from around the delivery system 1 during a procedure is possible. In other embodiments, the loader tube 10 is made of a material that can be peeled apart by the physician, without any etches or score marks made in the loader tube 10.

Referring to FIGS. 12-22, a second embodiment of a loader assembly for loading a THV will be described. Similar to the loader assembly discussed with respect to FIGS. 1-11, the loader assembly in FIGS. 12-22 is generally configured for use with heart valve prostheses that can be radially crimped to facilitate endovascular delivery to an implant site at a patient's heart. The loader assembly can be used to more easily and efficiently load the crimped valve into a patient's body through a delivery sheath device or system. However, in the embodiment in FIGS. 12-22, the replacement valve can be crimped directly on a balloon expander prior to insertion into the delivery sheath and before the balloon expander has been inflated, where the crimped prosthetic valve and balloon delivery system can be inserted into the delivery sheath at the access site of the patient, and then advanced to the implant site together.

Generally, prior to inserting a valve prosthesis into the patient's body, the valve is retrieved from a storage container or other packaging and prepped for implantation, is radially crimped or collapsed, and is then loaded into the patient's body through a sheath delivery system or other similar means.

Valve prostheses can be individually held in storage jars or containers prior to use. The storage jars generally hold the valve in a glutaraldehyde solution or other similar solution or compound that effectively keeps the valve preserved and sterilized during storage. Once a valve has been selected for implantation, the valve prosthesis is removed from the storage jar and the glutaraldehyde, and is flushed or washed with saline or other similar body-compatible solution. The valve is then placed in a separate crimping device, where radial pressures are applied on the valve to collapse the valve to its crimped orientation. Finally, the crimped valve is inserted through a separate loader tube for introducing the crimped valve into a patient's body through the delivery sheath. Since there are three separate devices for performing these three separate functions, preparation of THVs even prior to introducing the valves into the delivery sheaths is cumbersome and time consuming. Additionally, using so many separate preparatory devices, as well as having to transfer the valves between the respective devices, increases the likelihood and risk of making procedural or other preparatory errors.

According to embodiments of the invention, a loading assembly is utilized for loading the prosthetic heart valve into a pre-positioned delivery sheath or catheter at an access site on a patient. The system can be assembled together, such that a storage unit, a crimper, and a loader for the valve prosthesis can be combined into a single unit. By using such a loading assembly to prepare and introduce the valve prosthesis into a delivery sheath for implantation, preparation procedures for the valve prior to implantation can be combined and simplified, and the time associated with preparing and manipulating the valve to its crimped state prior to implantation can be reduced.

Figure 12:
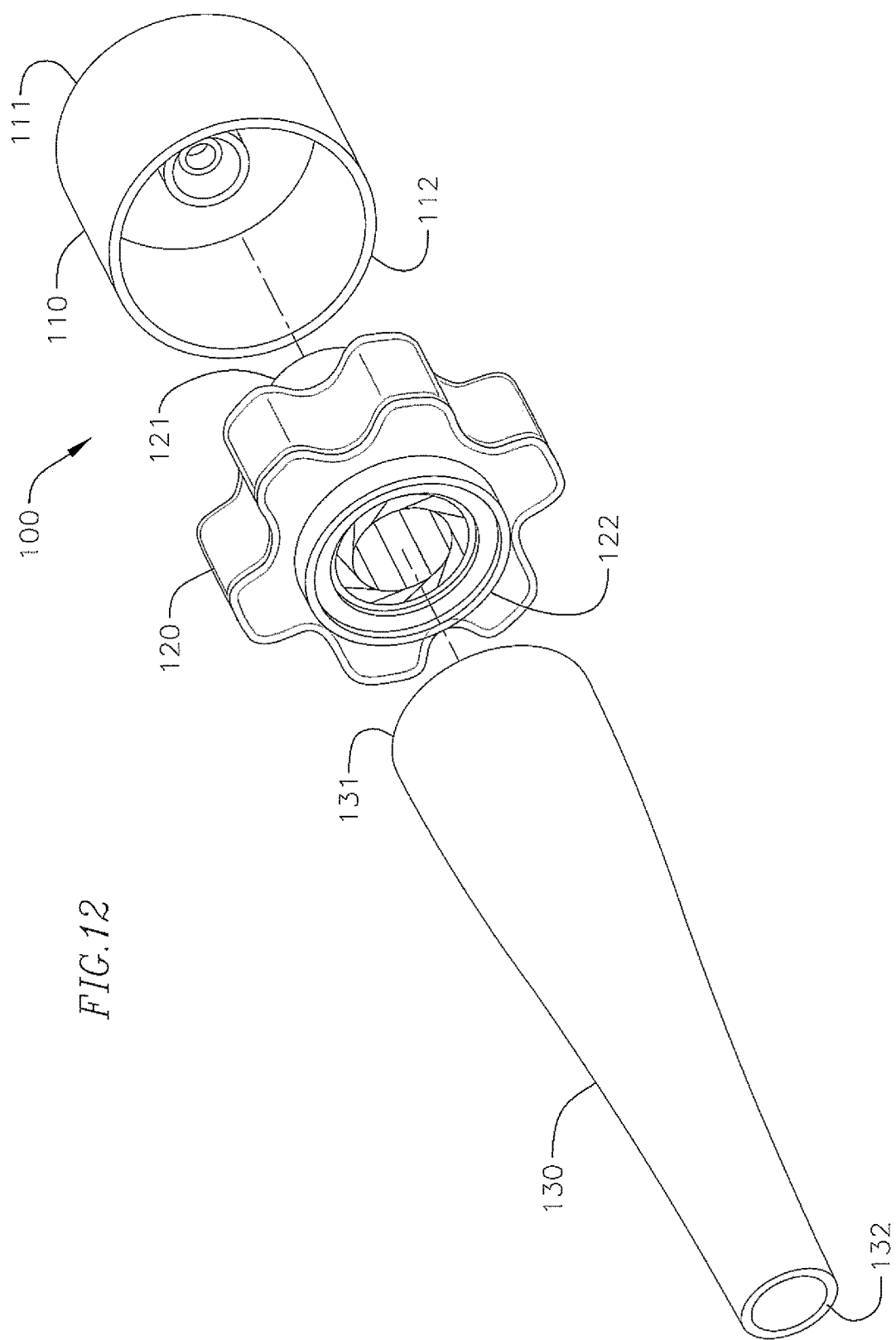
FIG. 12 shows an exploded perspective view of a loader assembly for loading a transcatheter heart valve into a delivery sheath, according to a second embodiment of the invention.

A loader assembly according to an embodiment of the invention is illustrated in FIGS. 12 and 13. The loader assembly 100 includes a storage jar or container 110, a crimping apparatus or crimper 120, and a loader tube 130. The storage container 110 has a first proximal end 111 and a second distal end 112. The distal end 112 of the storage container 110 is connectable to a proximal end 121 of the crimper 120, so that a valve prosthesis that is initially housed in the container 110 can be advanced directly into the crimper 120. The crimper 120 further has a distal end 122 that is connectable to the loader tube 130. The loader tube 130 has a proximal end 131 connectable to the crimper 120 and a distal end 132 with an opening configured to facilitate advancement of the crimped valve prosthesis into a delivery sheath or other delivery catheter.

Figure 14A:
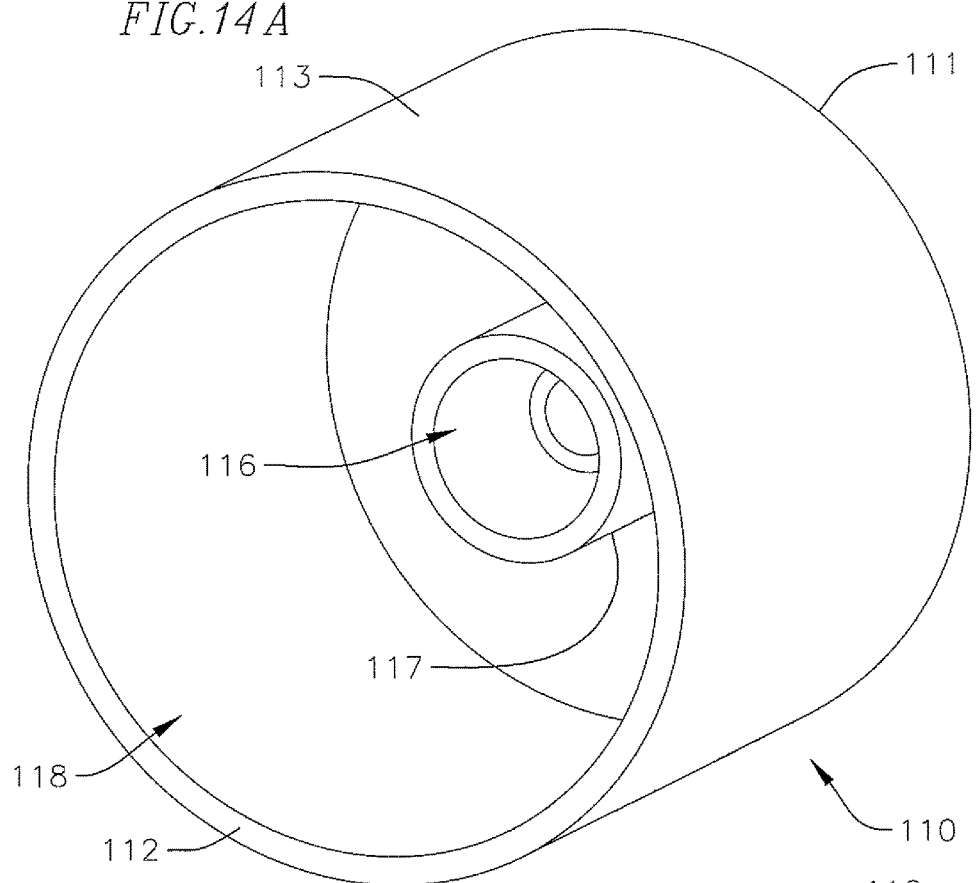
FIGS. 14A and 14B show a perspective view and a cross-sectional view, respectively, of a valve storage jar or container of the loader assembly according to the second embodiment.
Figure 14B:
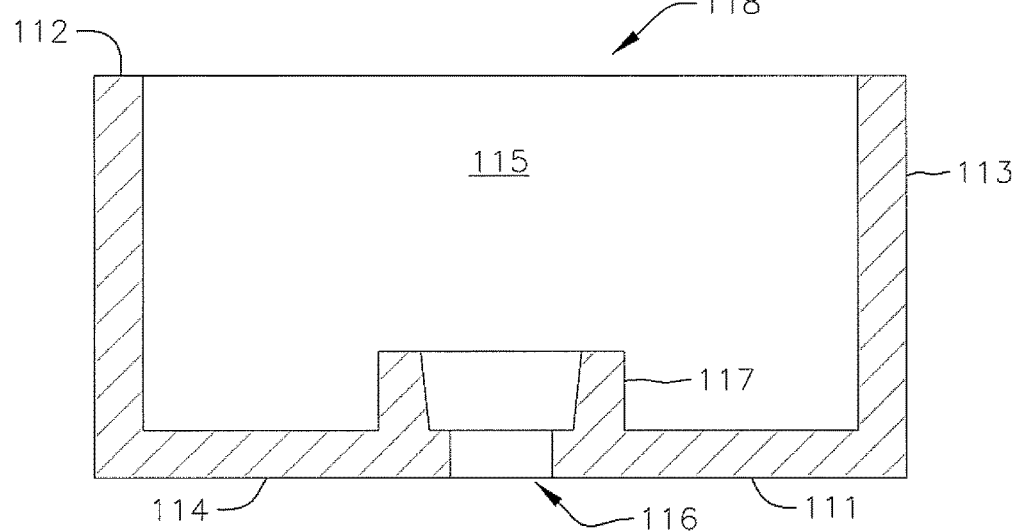

Referring to FIGS. 14A and 14B, the storage container 110 includes a generally cylindrical wall 113 extending between the ends 111, 112. In addition, at the proximal end 111, the container 110 has an end wall 114 that forms a base or bottom of the container 110. Together, the outer wall 113 and the end wall 114 define a generally cylindrical inner space 115 of the container 110. The space 115 has a diameter that is greater than a diameter of a fully expanded transcatheter heart valve to be held in the container 110. At a center of the end wall 114 is an opening 116 that facilitates access into the bore 115 from the proximal end 111 of the container 110. The opening 116 is sized to facilitate insertion of a collapsed balloon expander and a delivery catheter of a valve delivery system therethrough. In some embodiments, an annular ring 117 defines the opening 116 through the end wall 114 and projects slightly into the inner space 115 of the container 110. The slightly elongated annular ring 117 can serve, for example, as a guide for correctly loading a tip of the expandable balloon, or more generally a distal end of the delivery system, through a center of the expanded valve prosthesis held in the storage container 110, and/or for properly positioning the expandable balloon through the valve prosthesis prior to advancing the valve and balloon assembly into the crimper 120. At the distal end of the container 110, a second opening 118 is large enough for the expanded valve prosthesis to advance through. In some embodiments, an attachment feature (not shown) is provided on an inner surface or on an outer surface of the wall 113 at the opening 118 to facilitate attachment and/or sealing between the container 110 and the crimper 120. The attachment feature can be, for example, threads or a lip. Additionally, the same or different engagement features (not shown) can be provided adjacent one or both the opening 116 or the opening 118 for attaching caps or seals during valve storage, before the particular valve is selected for implantation.

Figure 15A:
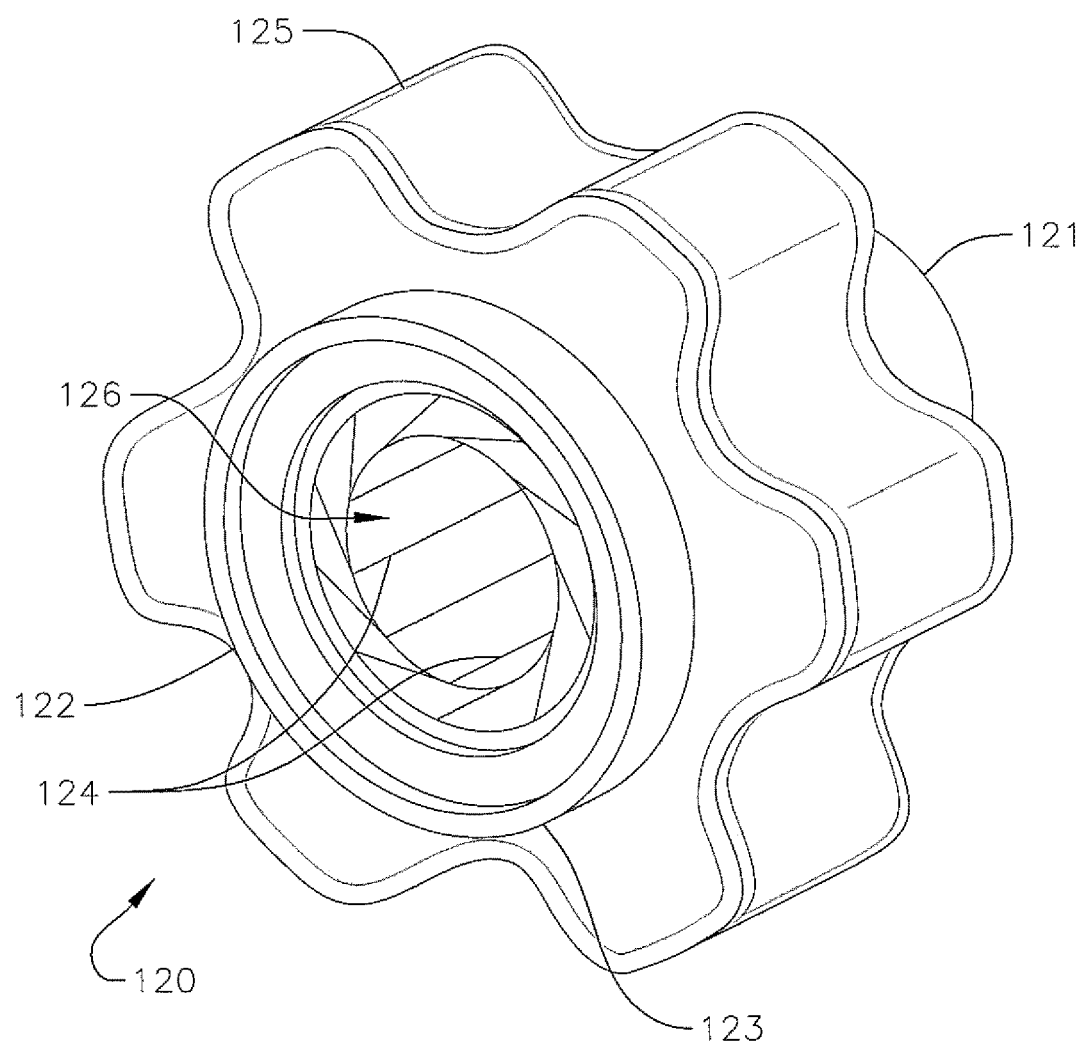
FIGS. 15A-15C show a perspective view, a side view, and a cross-sectional view, respectively, of a crimper tool of the loader assembly according to the second embodiment.
Figure 15B:
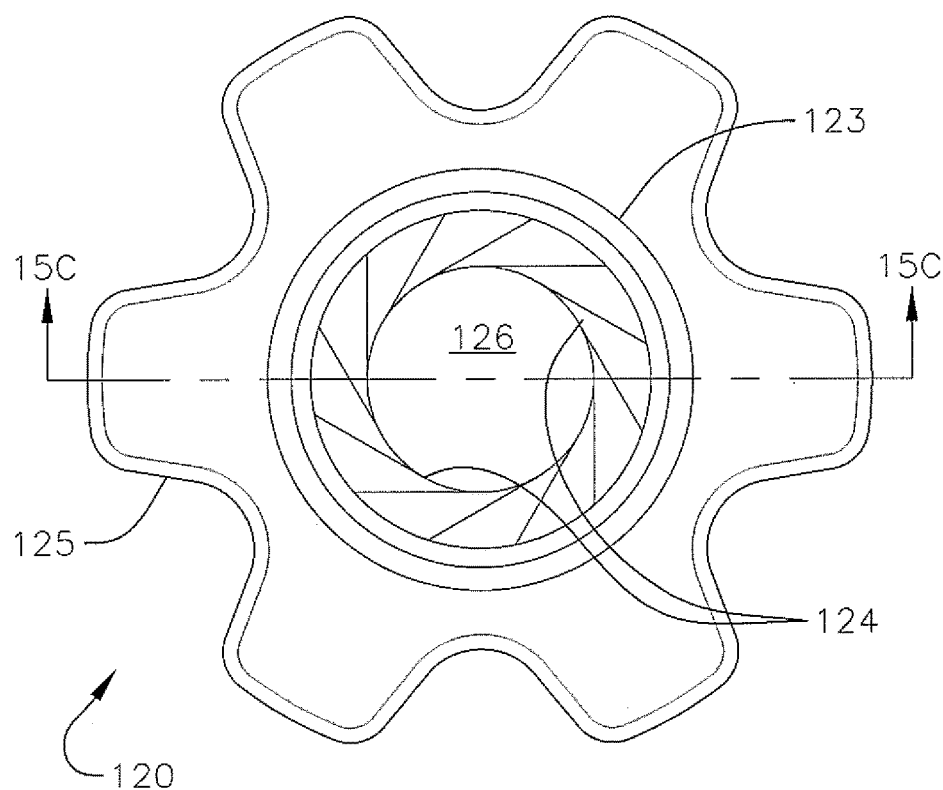
Figure 15C:
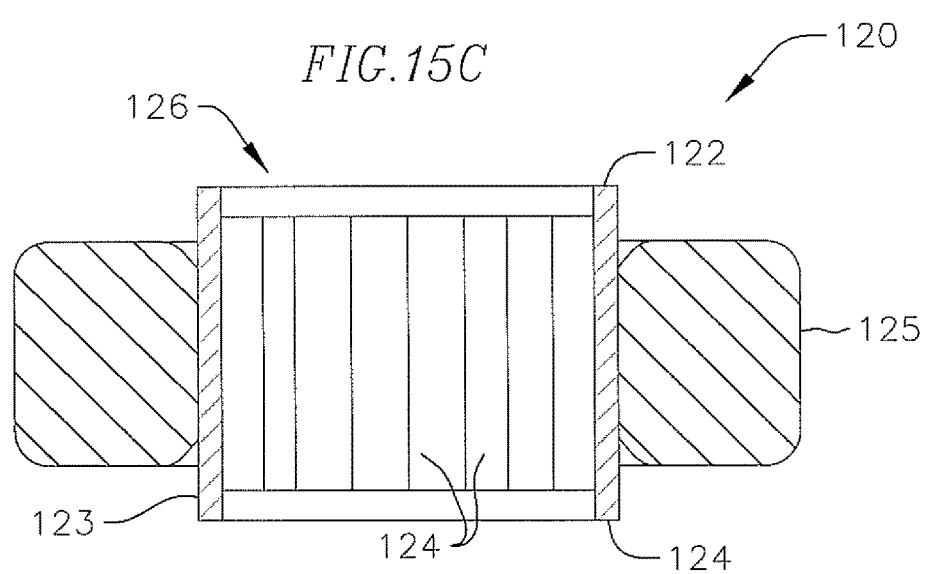

As can be seen in FIGS. 15A to 15C, the crimping apparatus 120 includes a generally tubular body 123 that extends from the first end 121 of the crimper 120 to the second end 122 of the crimper 120. An outer wall of the body 123 is generally cylindrical in the embodiment shown, and has openings at both the first and second ends 121, 122. The crimper 120 defines a central aperture or bore 126 that extends from the first end 121 to the second end 122 of the crimper 120. In some embodiments, either the outer surface and/or the inner surface of the body 123 can also include one or more engagement structures, such as threads (not shown), adjacent to either the first or second ends 121, 122, or both, for engaging other parts of the assembly. On an inner surface of the body 123, there is a crimping device for crimping a transcatheter heart valve. In the embodiment shown, the crimping device includes crimping jaws or a similar mechanism. The crimping jaws are formed by a plurality of wedges 124 which define a size of the central bore 126. The central bore 126 can be substantially cylindrical, to facilitate placement and crimping of the heart valve prosthetic therein. In the case where wedges 124 are used, the sides of the wedges can be substantially flat, so that a polygon with a number of sides equal to the number of wedges 124 is formed to approximate a cylindrical shape. The wedges 124 articulate relative to one another to increase or decrease a size of the central bore 126. In other embodiments, different known crimping mechanisms can instead be utilized in place of the wedges 124. Meanwhile, a handle or knob 125 circumferentially surrounds an outer surface of the tubular body 123. The knob 125 can be shaped to include indentations and/or other features that facilitate gripping and rotating around the body 123 by a user. The knob 125 is mechanically coupled to the wedges 124, such that rotation of the knob 125 in one direction will cause the wedges 124 to rotate relative to one another (e.g., in the same direction), in order to increase the size of the bore 126, while rotation of the knob 125 in the opposite direction will also cause the wedges 124 to rotate relative to one another in the opposite direction to decrease the size of the bore 126. In some embodiments, the crimper 120 can be configured such that the bore 126 decreases in size and then subsequently increases in size in response to rotation of the knob 125 in the same direction, in order to simplify operation.

Referring now to FIGS. 16A and 16B the loader 130 also includes a generally tubular body 133 that extends from a first end 131 of the body 133 to a second end 132 of the body 133, and that defines an inner bore 134. The first end 131 of the body can include an engagement structure (not shown) for engaging the crimper 120. The engagement structure can be on an outer surface or an inner surface of the loader tube 130, in order to complement a corresponding engagement structure on the crimper 120. The loader tube 130 is utilized to correctly orient and position the heart valve before the heart valve is advanced into, for example, a catheter or expandable sheath that has already been positioned in a patient's body, and in some cases, can also further reduce a size of a crimped transcatheter heart valve. As such, the inner bore 134 of the loader tube 130 gradually reduces in diameter from the first end 131 to the second end 132, where a size of the opening at the second end 132 can be configured to be slightly larger than a desired diameter of the transcatheter heart valve after it has been crimped (e.g., by crimper 120), or correspond to a diameter of a crimped valve prosthesis that is desired for delivery through the patient's body.

Figure 17:
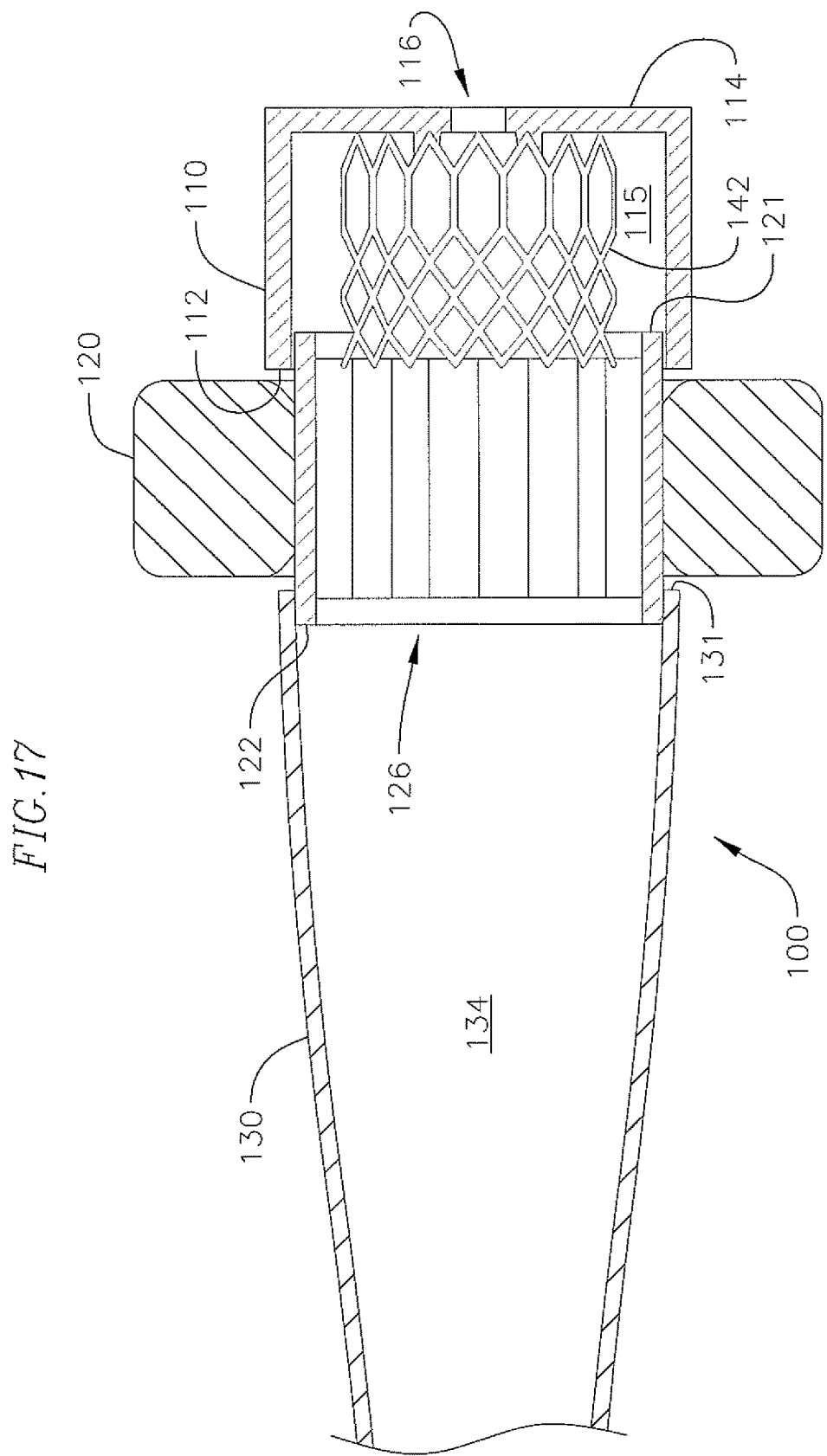
FIGS. 17-22 illustrate steps of advancing a transcatheter heart valve through the loader assembly according to the second embodiment, and of crimping the heart valve using the loader assembly according to the second embodiment, to prepare the heart valve for implantation.

FIGS. 17-22 illustrate a method of utilizing the loader assembly 100 for preparing, crimping, and advancing a THV for delivery through a patient's body via a delivery catheter or sheath. Prior to assembling the various parts of the loader assembly 100 as illustrated in FIG. 17, the THV can be stored in the storage container or housing 110. Various sealed storage containers 110 can, for example, hold different sized or different shaped THVs 142, and can be labeled for easy identification by a practitioner. Prior to use, each of the storage containers 110 can be sealed at both ends, with for example, a plug or cap at opening 116 (not shown) and a lid or cap at opening 118 (not shown). Once a suitable valve 142 is selected for a particular procedure, the storage container 110 holding the desired valve 142 is selected and unsealed, and the glutaraldehyde and/or other preservation/sterilization solutions are drained from the storage container 110. The inside of the container 110, including the valve 142, can also be washed or flushed with saline or other similar solutions to remove residual glutaraldehyde prior to implantation. This flushing step can be streamlined with, for example, tubes and/or stopcocks that easily connect to one or both ends of the storage container 110. In some embodiments, additional openings for more effective flushing and/or draining of the storage container 110, for example, on the sides of the container 110, can also be added.

Once the inside of the storage container 110, including the valve prosthesis 142, has been rinsed or flushed, the storage container 110 holding the valve prosthesis 142 can be attached to the first end 121 of the crimper 120. The loader tube 130 can be attached to the second end 122 of the crimper 120 before or after the storage container 110 has been attached to the crimper 120. As shown in FIG. 17, the storage container 110 is still holding the valve prosthesis 142, while a general pathway is formed between the inner space 115 of the storage container 110, the central bore 126 of the crimper 120, and the inner bore 134 of the loader tube 130, to facilitate advancement of the valve prosthesis 142 and the associated delivery system through and out of the distal end of the loading assembly 100, via the opening at second end 132 of the loader tube 130. As shown in FIG. 17, the wedges 124 of the crimper 120 are arranged so that the bore 126 has a greater diameter than a diameter of the valve prosthesis 142 in an expanded configuration, to facilitate advancement of the valve prosthesis 142 into the crimper 120 prior to being crimped.

Figure 18:
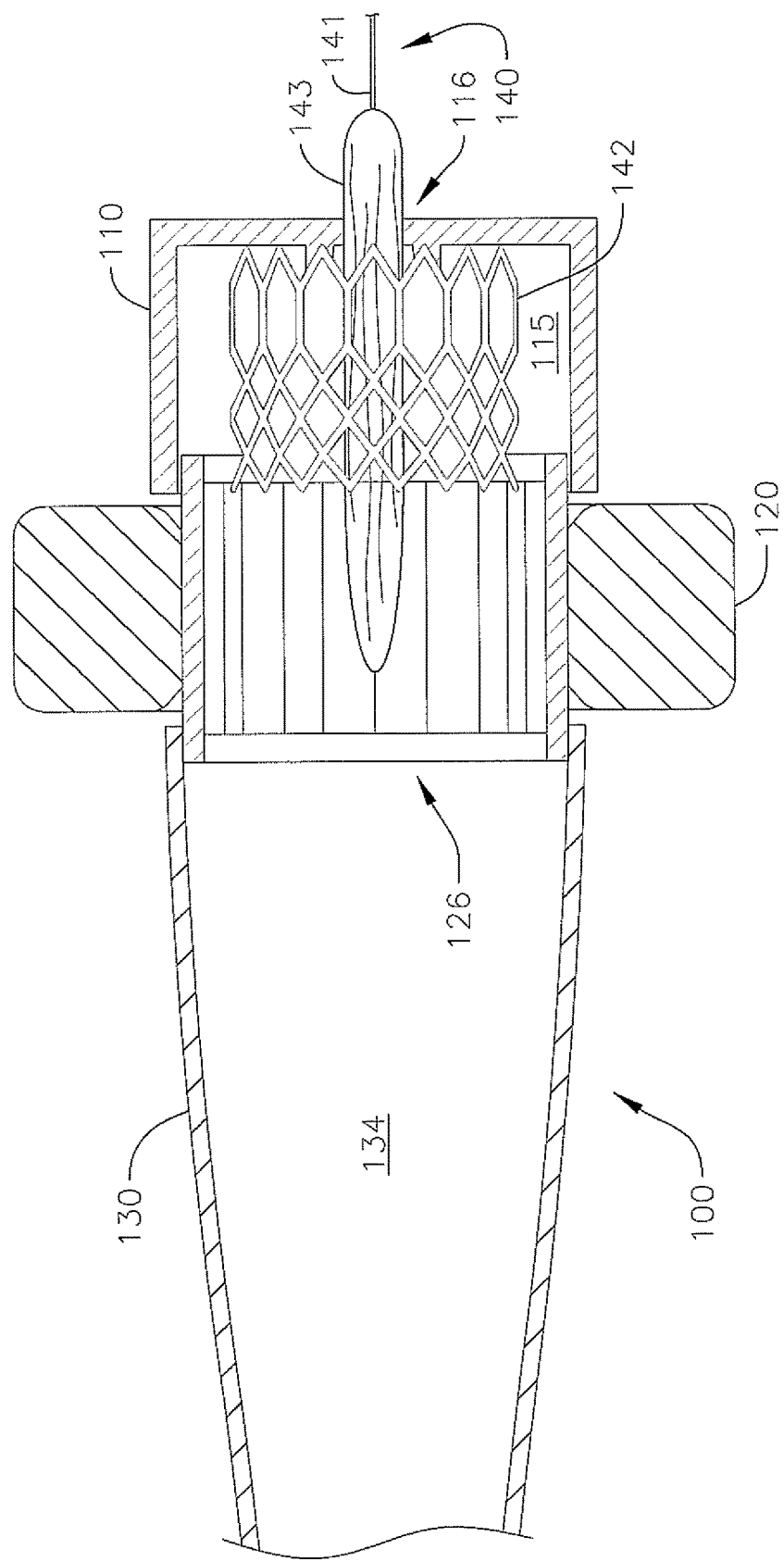

In FIG. 18, a delivery system 140 is advanced into the loading assembly 100. The delivery system 140 can include a delivery catheter 141 and an expandable balloon 143 positioned at or attached to a distal end of the delivery catheter 141. An additional guide wire (not shown) can further be positioned at a distal end of the expandable balloon 143. The delivery system 140 can be advanced through the opening 116 of the storage container 110, where the opening 116 is sized to permit insertion of the expandable balloon 143 when it the balloon 143 is in a deflated or unexpanded state.

Figure 19:
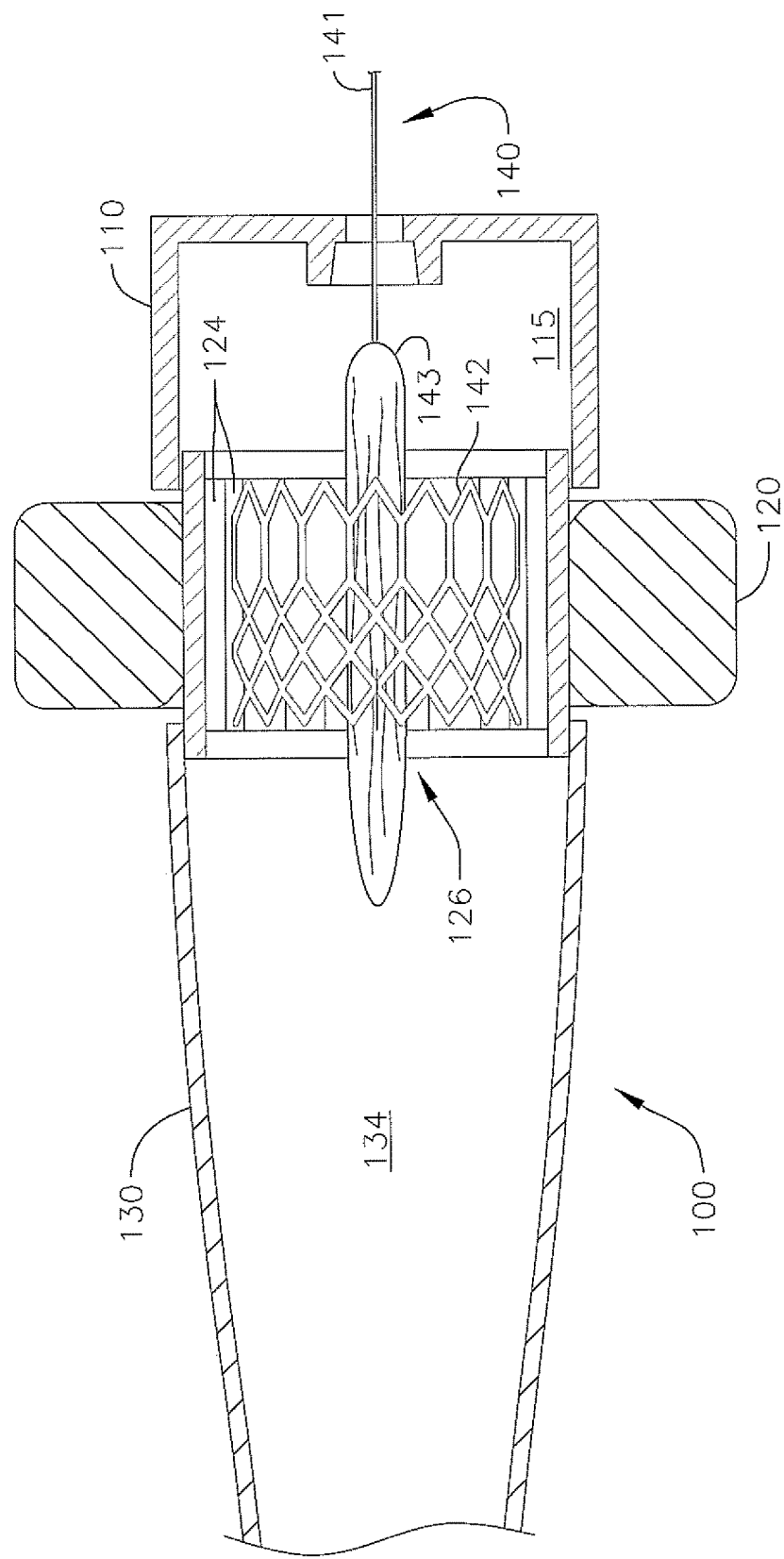

Upon insertion of the balloon 143 through the opening 116 of the storage container 110, the balloon 143 engages the valve prosthesis 142. In some embodiments, the balloon 143 engages valve leaflets of the valve prosthesis 142, and can be sized and shaped so that upon engagement or attachment with the valve prosthesis 142, the engagement is strong enough to advance the valve prosthesis 142 together with the balloon 143 out of the storage container 110 and into the bore 126 of the crimper 126, as seen in FIG. 19. In some embodiments, an additional engagement feature or accessory can be added on either the balloon 143 or the prosthetic valve 142 (not shown) to more readily facilitate proper engagement between the respective parts. In other embodiments, a frictional force between the balloon 143 and the valve prosthesis 142 is sufficient to facilitate the engagement. In still other embodiments, the valve prosthesis 142 can instead attach to and be crimped along a shaft of the delivery catheter 141, or to another portion of the delivery system 140 other than balloon 143, based on the needs and specific operation of the particular delivery system. Alternatively, the loader tube 130 can be detached, or can remain detached, from the crimper 120, until a desired positioning of the valve prosthesis 142 and/or the delivery system 140 in the crimper 120 is achieved when viewed from the distal end 122 of the crimper 120.

Figure 20:
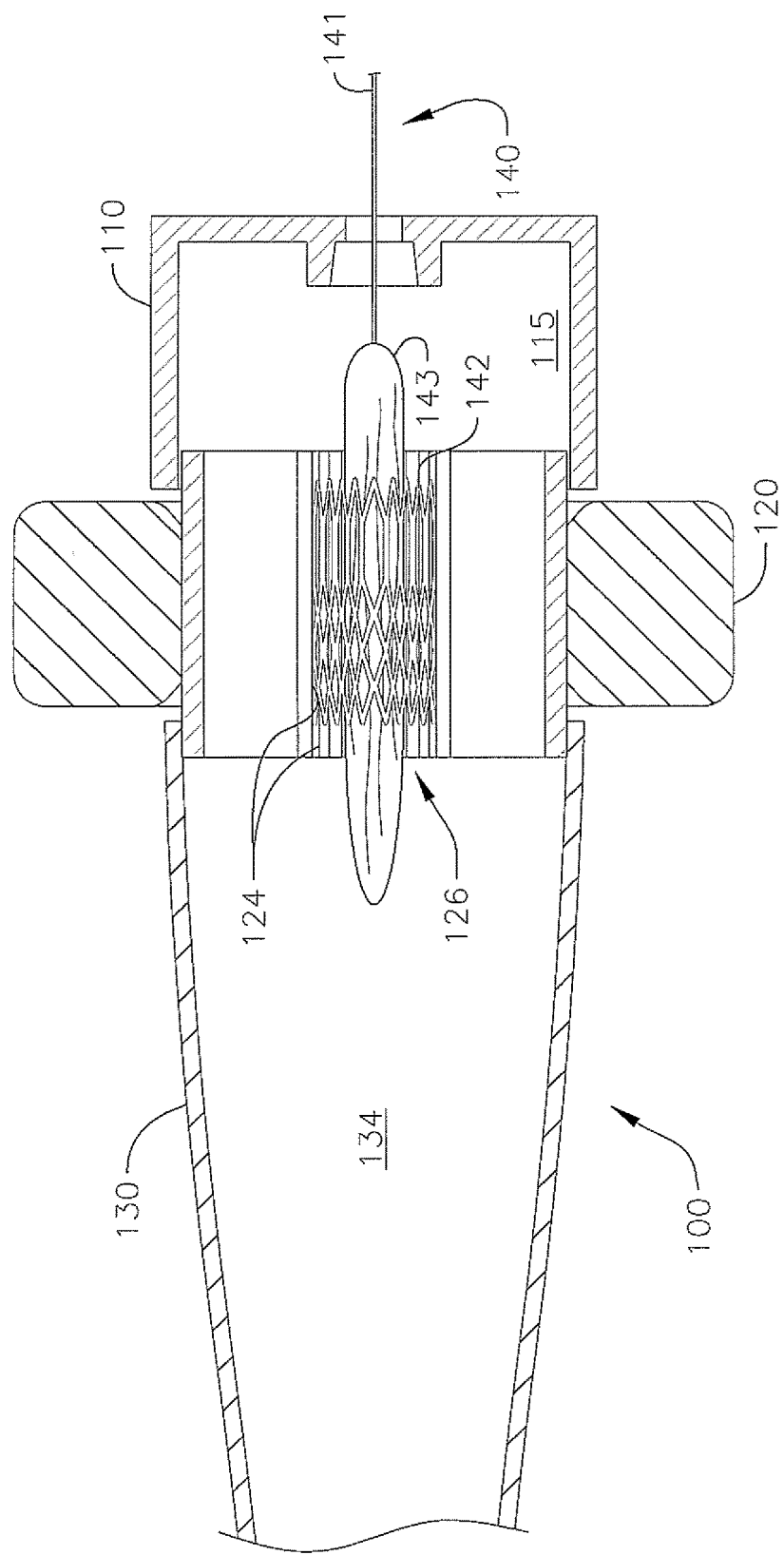
Figure 21:
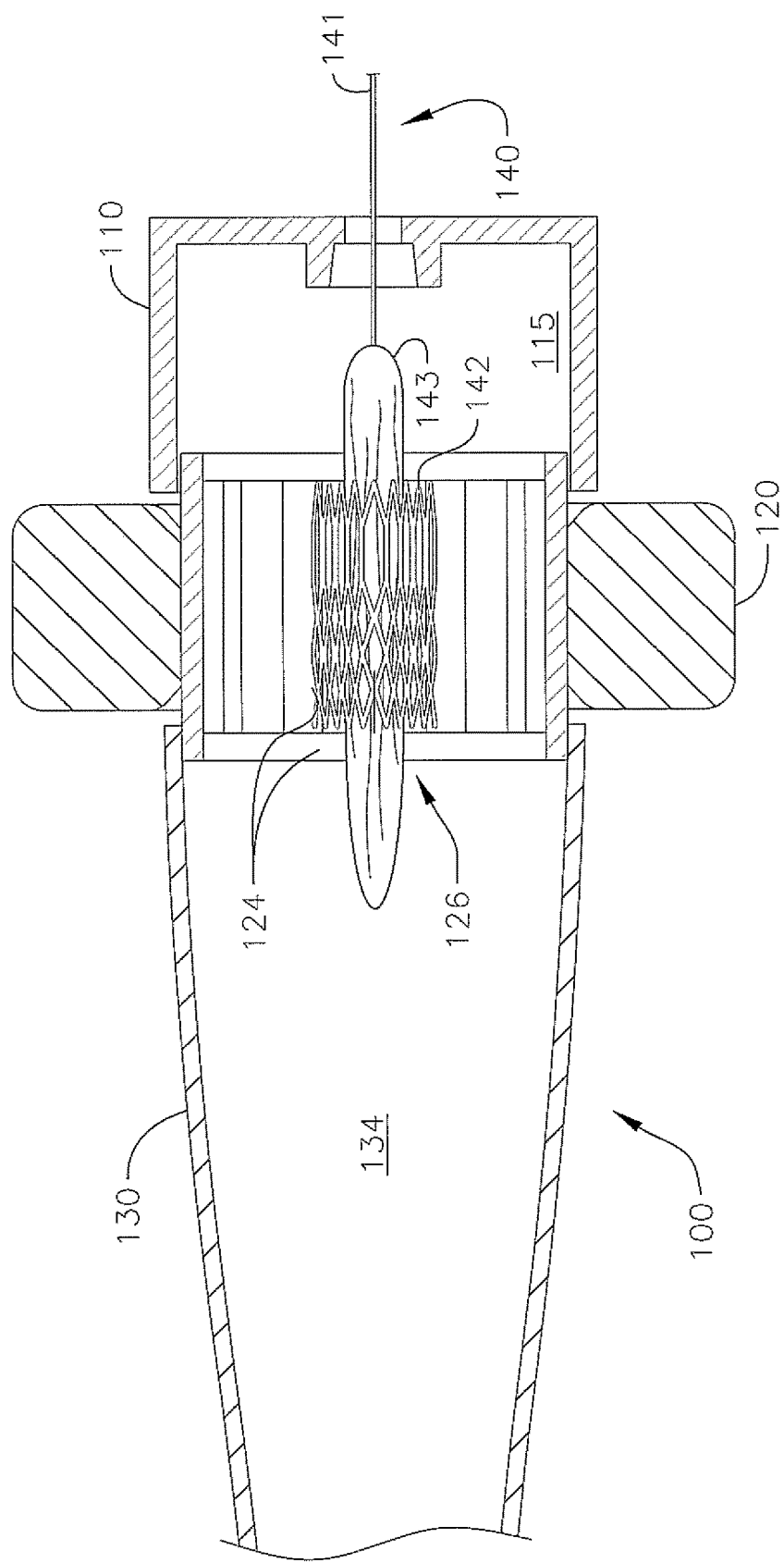

In FIGS. 20 and 21, the valve prosthesis 142 and the balloon 143 are still positioned in the bore 126 of the crimper 120. First, in FIG. 20, the knob 125 on the crimper 120 is turned or rotated about the loading assembly 100 by an end user, in order to rotate the wedges 124 relative to one another for making the bore 126 smaller. The sides of the wedges 124 apply inward radial pressure on the valve prosthesis 142 during articulation, in order to crimp the valve prosthesis 142 to a required or desired crimped or collapsed configuration. Thereafter, in FIG. 21, the knob 125 on the crimper 120 is turned in order to make the wedges 124 shift back towards their original positions, in order to increase the size of the bore 126 in the crimper 120. Meanwhile, the valve prosthesis 142 remains in the collapsed or crimped state around the balloon 143 or another corresponding portion of the delivery system 140. In other embodiments, different mechanisms can be used to crimp the valve prosthesis 120 via various alternative types of crimpers.

Figure 22:
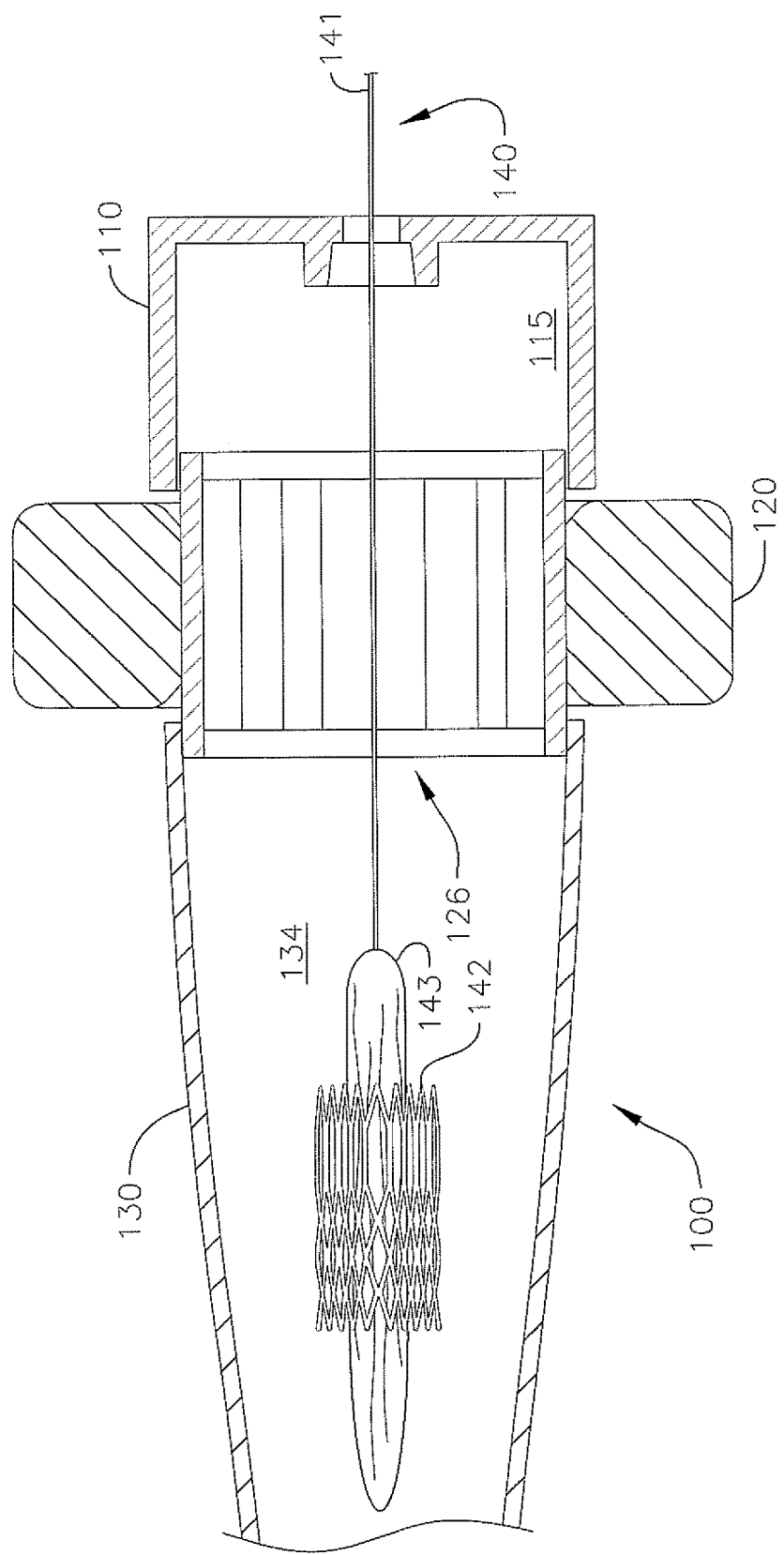

Once the valve prosthesis 142 has been crimped and the bore 126 of the crimper 120 has been expanded back to or near its original expanded size, the delivery system 140 along with the valve prosthesis 142 can be pushed or otherwise advanced to the loader tube 130, as seen in FIG. 22. A distal end 132 of the loader tube can be inserted into, for example, a delivery sheath or catheter that is already positioned in and provides access to a patient's body. The loader tube 130 directs the delivery system 140 and the crimped valve prosthesis 142 out through the opening at the distal end 132 of the loader tube 130 and into the delivery sheath or catheter, and thereafter the valve prosthesis 142 and delivery system 140 can be advanced to a desired implant site in the patient's body.

In prior situations, various different parts, such as separate jars or storage containers, crimping devices, and loader tubes were needed for preparing a transcatheter heart valve for implantation. Various other parts or assembly devices were also utilized based on each particular clinical situation. The loader assemblies according to embodiments of the invention combine three assembly devices into a single integral and easy to use loading device. In some embodiments, different storage containers and/or crimpers can be designed or modified to better interact with one another, and with different loader tubes. In some embodiments, the crimper is designed to interact and connect with and/or seal to an existing loader tube, such that a pre-existing loader tube can be used with the other parts of the loading assembly, without significantly modifying the loader tube.

Furthermore, the loader assembly according to embodiments of the invention can be designed to interact with other components used to prepare the valve prosthesis in various other ways, also without having to modify the other devices. For example, the loading assembly can be made to be compatible with existing delivery systems, including existing balloon expanders and delivery catheters. The loading assembly can also be designed to be compatible with other preparatory features or kits, such as the Edwards Qualcrimp™ crimping accessory, or other accessories that, for example, protect the leaflets from pinching on the frame or portions of the crimping tool during valve crimping. Furthermore, while the described loading assemblies are discussed using storage containers that store valve prostheses in glutaraldehyde solutions or similar storage solutions, loading assemblies in other embodiments can be used with dry tissue valve technology or storage devices. In addition, instead of using shelf stored valves (e.g., valves that are stored in expanded configurations), the loading assembly can also be used with valve prostheses that are held or stored in other configurations, for example, valves that have been pre-crimped. Various other features and/or modifications can also be envisioned in other embodiments to accommodate other variations in valves or clinical needs. In this manner, loading assemblies according to embodiments of the invention can simplify the pre-implantation procedure, reduce possible errors, and make preparation easier and less time consuming for the end user.

A method for crimping a THV according to another embodiment of the invention will now be discussed with reference to FIGS. 23-28. While previous embodiments of the invention focused on loading assemblies for preparing and loading a THV into a patient's body, the following method focuses on methods of preparing and packaging a THV prior to delivery to a practitioner or other end user.

Ideally, to reduce preparatory work and to simplify the valve implanting procedure for the end user, and to reduce possible errors by the end user that could potentially damage a valve prosthesis during crimping, it would be desirable to be able to package THVs in their fully crimped configurations and already pre-positioned on a balloon delivery system, so that the valve prosthesis is ready to implant upon opening or removing from storage. However, storing THVs in their crimped or collapsed positions has been found to cause deformation or deterioration of the valve leaflets, and generally reduced performance by the valve leaflets once the valve prosthesis is expanded. Therefore, transcatheter valve prostheses are still generally stored in an open or expanded configuration, and are crimped or collapsed by a practitioner or other end user just prior to implantation into a patient's body, so that the valve prostheses are held in their crimped states for a limited amount of time (e.g., only during delivery of the valve to the implant site).

Recently, research has been devoted to providing THVs that can be packaged or stored directly on balloon and in their crimped states, without damaging or reducing the performance of the valve leaflets. Various treatments could potentially allow for packaging and sterilization of the prosthetic valve in a dry condition, e.g., without the need for a liquid storage solution, which could obviate the need to rinse or otherwise prepare the valve prior to implantation. Some treatments under development focus on providing additional protection for the valve tissue by enhancing anti-calcification properties and improving durability of the valve tissue. However, after crimping and packaging THVs using such dry tissue packaging or other similar dry tissue preparatory processes, problems or issues such as tissue shrinkage and/or other deformation of the leaflets may occur, and as such, the long-term effects these changes would have on the functionality of the THVs remain unknown. For example, studies have shown that exposure to ethylene oxide during sterilization of dry-packaged valves in their crimped states causes approximately 25% shrinkage to the widths of the valve leaflets. Other factors, such as dry packaging conditions or temperature conditioning parameters, can also contribute to tissue shrinkage or degradation.

In an alternate approach, research has been devoted to dry packaging prosthetic valves in their expanded states, together with a low-cost crimping or loading device that is preloaded with each valve, so that an end user can remove the valve with the preloaded crimper from packaging, position the balloon or other portion of the delivery system through the valve, crimp the valve just prior to implantation, and remove and discard the preloaded crimper. In this manner, preparing a THV for implantation can potentially be simplified for the end user. Furthermore, since the valves are stored in their expanded states, the issues with tissue shrinkage or other deformation of the leaflets can potentially be avoided or minimized.

However, this approach has also been met with its own set of drawbacks. Current crimping techniques involving full-size crimping apparatuses typically also require complicated preparation, engagement, and use of a protective sheath or similar crimping accessory to be placed between the prosthetic valve and the crimping apparatus, to assist in the crimping of the prosthetic valve and to protect the leaflets, for example, from pinching against the valve or the frame of the crimping tool during crimping. One such crimping tool is the previously mentioned Edwards Lifesciences Qualcrimp™ crimping accessory. While preloading prosthetic valves with a preloaded or "smart" loader or crimping device can potentially simplify the preparation process for the end user, currently developed preloaded crimping devices still require use of the complex protective crimping accessories for protecting the valve leaflets when the valves are crimped by the end user. As such, the currently developed crimping devices and processes may only be marginally better and/or easier to use than their full-sized counterparts, or do not improve or simplify the process for the end user at all, while increasing manufacturing costs.

According to embodiments of the invention, a method and apparatus for crimping a THV during manufacturing and packaging is provided, so that preparation by an end user is simplified, and possible damage to or deformation of the prosthetic valve can be reduced or minimized. By using the crimping method described herein, a preloaded crimper or loader can be packaged with the valve prosthesis and utilized by the end user prior to implantation, without the need for an additional protective crimping accessory. Furthermore, the crimping method can be applied to valve prostheses with leaflets that have been treated for dry packaging, where the crimping method does not result in shrinkage of the leaflet tissue during packaging or storage of the valve before use. Lastly, the crimping method can be performed on a delivery balloon or other desired portion of a delivery system, to further simplify the preparation process for the end user. In this manner, the end user need only remove the assembly from the packaging, hydrate and/or sterilize the assembly, and then complete the crimping of the valve prosthesis before implanting the valve.

Figure 23:
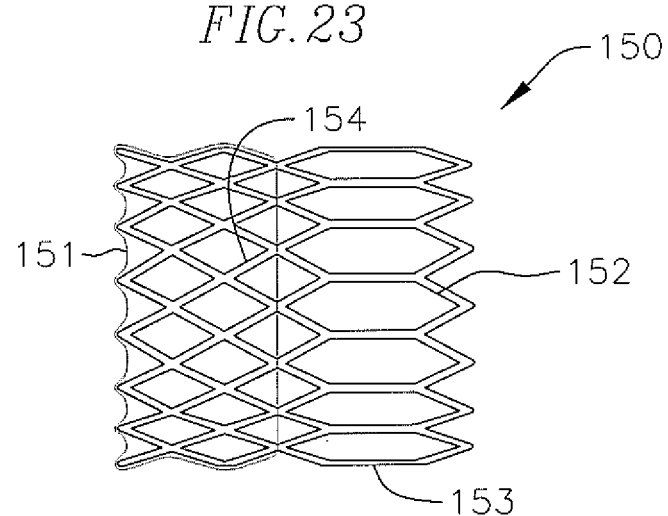
FIG. 23 shows a schematic side view of a transcatheter heart valve for use with a crimping method according to another embodiment of the invention.

A schematic side view of a THV to which the crimping method according to embodiments of the invention can be applied is illustrated in FIG. 23. The valve prosthesis 150 has an inflow section 151 and an outflow section 152. The valve prosthesis 150 includes a valve frame 153 that is generally cylindrical in shape and defines a bore extending between the inflow section 151 and the outflow section 152. The valve frame 153 is collapsible and expandable, so that the outer profile of the valve prosthesis 150 can be reduced to facilitate delivery of the valve prosthesis 150 to an implant site of a patient, and can thereafter be increased for anchoring the valve prosthesis 150 at the implant site. Expansion of the valve frame 153 also increases the diameter of the bore through the valve prosthesis 150, and deploys the valve leaflets therein to a final configuration or arrangement for regulating blood flow at the implant site. For simplicity of discussion, the valve leaflets have not been illustrated in the schematic valve illustrations in FIGS. 23-28. In addition, an outer skirt or other covering 154 can cover at least part of the valve frame 153. The outer skirt 154 can seal gaps between the valve prosthesis 150 and the native valve annulus at the implant site to reduce or prevent paravalvular leakage, and can also protect the surrounding tissue at the implant site after implantation. In the embodiments shown, the outer skirt 154 covers a portion of the inflow section 151 of the valve prosthesis 150. The outer skirt has been illustrated in FIGS. 23-28 as being a transparent layer, so that the portions of the valve frame 153 covered by the outer skirt 154 can be seen. However, in other embodiments, the outer skirt 154 can instead be made of materials such as fabric that are translucent or opaque.

The valve frame 153 of the THV 150 is designed with two or more rows of diamond-shaped cells at the inflow section 151 and one row of elongated hexagonal-shaped cells at the outflow section. The valve frame 153 is designed to reduce a delivery profile of the valve prosthesis 150, while being able to maintain radial strength in the valve upon expansion, among other features and properties. One example of a THV with a similar valve frame profile is the Edwards Lifesciences SAPIEN 3™ transcatheter heart valve. However, the crimping methods according to embodiments of the invention are not intended to be limited to prosthetic valves with frames similar to the ones discussed with respect to FIGS. 23-28, but rather can generally be applied to any THV with issues similar to those discussed above.

Referring back to the valve prosthesis 150 illustrated in FIG. 23, in some instances, the variations in frame cell shapes can contribute to different levels of stretching of the valve leaflets that are housed inside the valve frame. For example, when the valve 150 is fully crimped, the diamond-shaped cells at the inflow section 151 of the valve prosthesis 150 can contribute to greater axial stretching of the valve leaflets than the hexagonal-shaped cells at the outflow section 152 of the valve prosthesis 150. Such differences in leaflet tissue stretching can lead to additional stresses on the leaflets during packaging or storage if a valve prosthesis 150 is stored for extended periods in its crimped state. Consequently, shrinkage or other dimensional deformations of the leaflet tissue can be more severe at the inflow section 151 than at the outflow section 152 of the prosthetic valve 150 if the prosthetic valve 150 is stored in the crimped state. In some instances, the shrinkage or other deformation of the leaflet tissue may occur only at or near the inflow section 151, while deformation of the leaflet tissue at or near the outflow section 152 is minimal.

Figure 24:
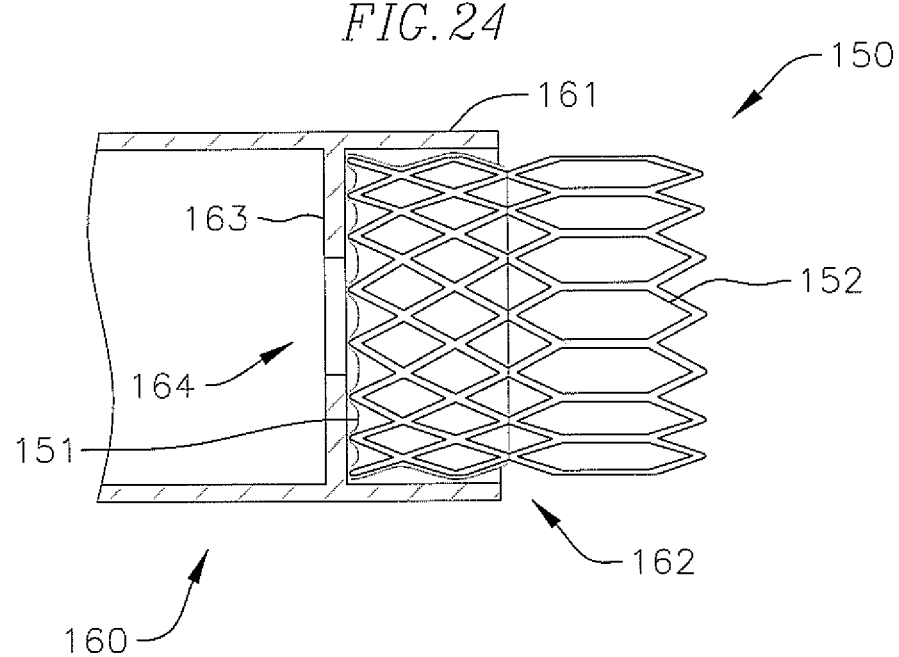
FIGS. 24-26 illustrate steps of crimping the transcatheter heart valve of FIG. 23 according to an embodiment of the invention.

FIG. 24 illustrates a first step of a crimping method according to an embodiment of the invention. As noted above, the crimping method can be employed during manufacturing or packaging of THVs, so that an end user receives the prosthetic valves after the crimping method has already been completed. In FIG. 24, the THV 150 is inserted into a crimping fixture or holder 160. The holder 160 has an outer wall 161 that defines an opening 162 into which the valve 150 is inserted. The opening 162 can be slightly larger than a size of the prosthetic valve 150 in its expanded state, so that the valve 150 can be held snugly in the holder 160. The valve is held in the holder 160 such that at least a portion of the outflow section 152 of the valve 150 still protrudes out of the holder 160. In some embodiments, a portion of the inflow section 151 also protrudes out of the holder 160. The holder 160 can be constructed with, for example, an inner wall or annular ridge 163 that serves as a stop for the valve 150, so that when the end of the valve 150 at the inflow section 151 abuts the wall or ridge 163, a desired amount of the outflow section 152 of the valve 150 (and in some embodiments, a part of the inflow section 151 as well) remains exposed to the outside of the holder 160. The wall or ridge 163 can also define a central through bore 164, to be discussed in greater detail below.

Figure 25:
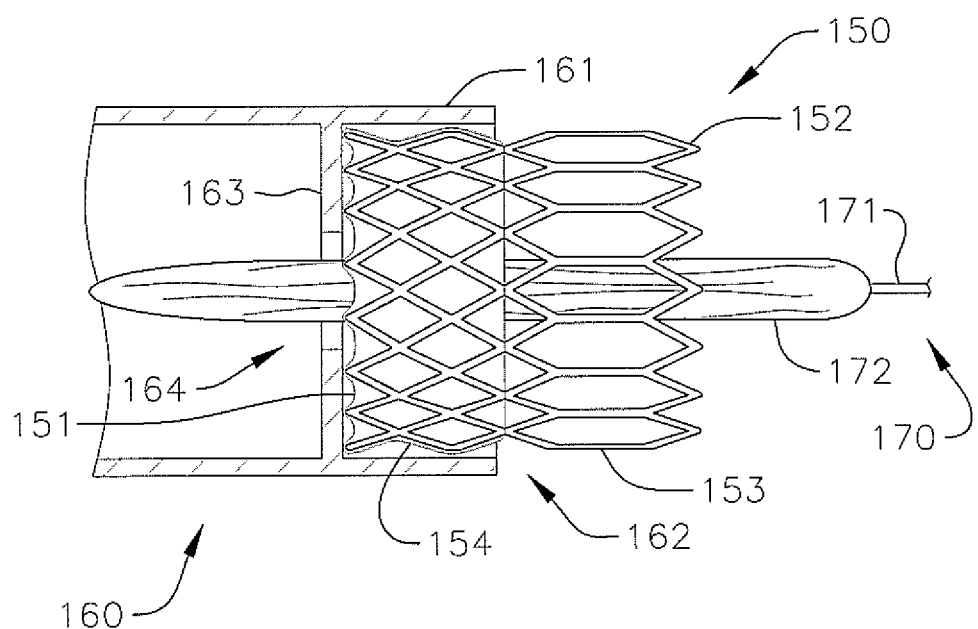

In FIG. 25, the exposed portions of the prosthetic valve 150 outside of the holder 160 are covered by a protective sheath or other protective crimping accessory (not shown). A delivery system 170 is then inserted through the THV 150 to a desired position. The delivery system can include a delivery catheter 171 and a balloon 172. The valve 150 can generally be crimped on the balloon 172 before the balloon 172 is expanded, but can also be crimped on any other suitable or desired portion of the delivery system 170. In embodiments where the holder 160 is hollow, or where the inner wall or ridge 163 includes the through bore 164, the balloon 172 can be advanced through the holder 160, such that a distal end of the balloon 172 can extend past a distal end of the valve prosthesis 150, to facilitate more versatile positioning of the balloon 172 relative to the valve prosthesis 150. In some embodiments, the valve 150 can be crimped off-balloon, so that the valve 150 is not crimped on the delivery system.

Figure 26:
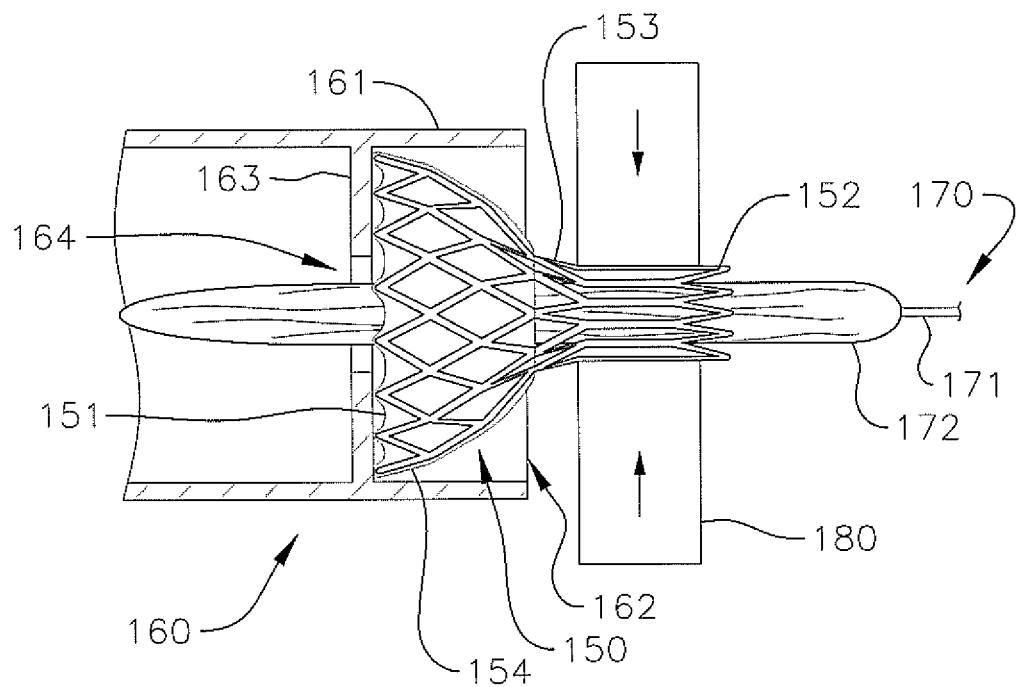

In FIG. 26, the exposed portion of the heart valve 150, along with the protective crimping assembly, are inserted into a bore or aperture of a crimping tool 180 until the end of the holder 160 is near to or abuts against the crimping tool 180. In some embodiments, for ease of manufacturing, the valve prosthesis 150 is first positioned through one end of the aperture of the crimper 180, and the balloon 172 of the delivery system 170 is then inserted through the valve prosthesis 150 via the other end of the aperture of the crimper 180 and arranged in a desired position prior to crimping of the valve prosthesis 150. The crimping tool 180 is then actuated to reduce the size of the aperture around the exposed portion of the valve 150 (e.g., as illustrated by the arrows in FIG. 26), in order crimp the exposed portion of the valve 150. The valve prosthesis 150 is crimped until the inward pressure from the crimping tool 180 is limited or stopped, for example, by the protective crimping assembly positioned around the valve prosthesis 150. In this manner, the crimping assembly can ensure that the prosthetic valve 150 is correctly positioned around and is coaxial with the balloon 172 or other suitable portion of the delivery system 170, and damage to the valve leaflets during crimping can be avoided. The aperture of the crimper tool 180 is then expanded, the entire assembly is removed from the crimper, and the holder 160 and protective crimping assembly (not shown) can be removed from around the valve 150, so that the heart valve 150 and delivery system 170 remain and can be packaged for delivery to an end user.

Figure 27:
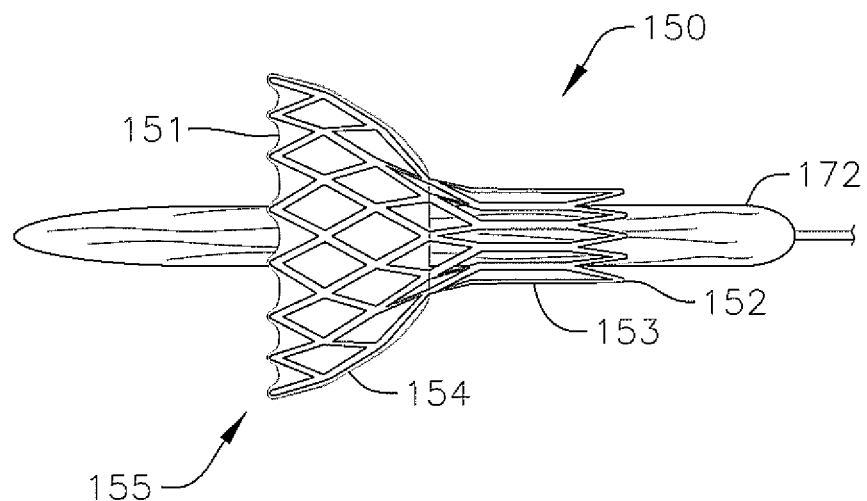
FIG. 27 shows a schematic side view of a transcatheter heart valve positioned and partially crimped on a balloon delivery system after applying the crimping method shown in FIGS. 24-26.

The resulting assembly, as illustrated in FIGS. 26 and 27, includes a partially crimped THV 150 that is crimped in a generally conical or tapered shape and positioned on a balloon catheter delivery system 170. The portion of the valve prosthesis 150 that was exposed outside of the holder 160 is crimped by the crimper to its collapsed state, while the portion of the valve prosthesis 150 that was held in the holder 160 remains in the expanded state. A transition region between the expanded and crimped portions of the valve 150 can form a substantially tapered or rounded conical shape. Upon partial crimping of the prosthetic valve 150, the valve leaflet tissue is still folded or collapsed down, but stretching of the leaflet tissue in an axial direction can be reduced or minimized (e.g., since the diamond-celled portions of the valve frame 153 are not significantly stretched out) to reduce stress on the valve leaflets during storage.

Figure 28:
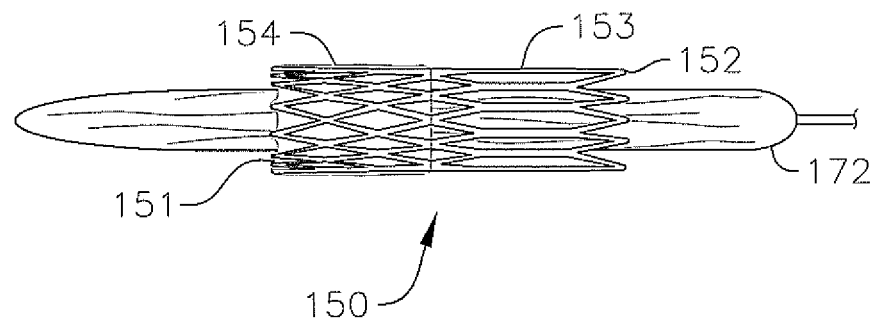
FIG. 28 shows a schematic side view of the transcatheter heart valve and balloon delivery system, where the heart valve has been fully crimped on the balloon of the delivery system.

In some embodiments, a preloaded crimper or loader can be placed around at least the remaining expanded portion of the valve prosthesis 150, and the assembly can be packaged together, so that an end user can easily remove the packaging, hydrate and/or sterilize the assembly, and use the preloaded crimper to crimp the rest of the prosthetic valve 150 to its fully crimped state around balloon 172 (e.g., as schematically illustrated in FIG. 28) in preparation for delivery through the patient's body. In some embodiments, additional packaging steps can be applied to further simplify the end user preparation process. Various other ways of packaging the assemblies can also be implemented, for example, to increase shelf life or better protect the valve prostheses during storage, to facilitate easier assembly or preparation by the end user, or based on various other specific needs or requirements of different practitioners and/or patients.

Using crimping methods according to embodiments of the invention, a THV can be partially crimped during manufacturing or packaging using a protective crimping assembly and/or other crimping tools. The prosthetic valve is crimped to a configuration where the protective crimping assembly is no longer needed to crimp the remainder of the prosthetic valve, so that the partially crimped prosthetic valve can be pre-packaged with a preloaded crimper, and without the need for the protective crimping assembly at the end user crimping step. Furthermore, the crimping method at the manufacturing stage can be tailored or adjusted to reduce or prevent shrinkage or other deformations of the leaflet tissues in the valve based on the specific characteristics of the leaflet tissues or the surrounding frame. For example, for the prosthetic valve 150, since the diamond-shaped cells at the inflow section 151 cause greater stretching of the valve leaflets than the hexagonal-shaped cells at the outflow section 152, and thereby lead to greater deformation of the leaflets if stored in the crimped state, portions of the inflow section 151 of the prosthetic valve 150 can be kept in the expanded or partially expanded state until the end user fully crimps the prosthetic valve 150.

Consequently, valves with leaflet tissue that have been treated or conditioned for dry packaging can be packaged in such a partially crimped manner to reduce occurrences of tissue deformation or shrinkage, thereby reducing the possibility of poor valve performance or valve malfunction. For example, in separate laboratory studies, THVs were held in fully crimped and partially crimped states, respectively, and were subjected to heat and ethylene oxide sterilization treatments, as well as shelf life tests including four weeks of aging at room temperature while crimped. The fully crimped valves were then hydrated and expanded, while the partially crimped valves were hydrated, were fully crimped without any additional crimping accessories to simulate the end user preparation and delivery process, and were then expanded. The valve leaflet tissue was removed from the respective frames and their dimensions were measured and further studied using a Keyence measuring system. While the leaflets from the fully crimped valves exhibited approximately 25% decreases in the top width and mid width dimensions compared to typical valves that were stored in their expanded states and only crimped prior to use, the dimensions of the leaflets of the partially crimped valves remained similar to those of their conventionally stored counterparts. Tissue shrinkage in the partially crimped valves was greatly reduced or unobserved when compared to the tissue shrinkage exhibited in the valves that were stored in their fully crimped states.

Valves according to other embodiments can be partially crimped in different ways. For example, where an outflow section of a prosthetic valve can cause more leaflet deformation, the outflow section can be kept expanded, while the inflow section can be crimped instead of the outflow section. In still other embodiments, the entire valve prosthesis can be crimped to varying degrees, where one or more sections is crimped more significantly than other sections, based on the particular properties of each transcatheter heart valve.

Using the manufacturing crimping methods described herein, there will be no need for additional protective sheaths or other extraneous crimping assemblies or tools that an end user will have to learn to use. This would be a significant improvement over the current crimping and preparatory processes that an end user has to perform. The crimping and packaging methods reduces the number of packaging components, reduces the number of preparatory steps needed prior to valve implantation, and reduces the number of operator-dependent skills that an end user needs. Simplifying the end user process will also reduce the potential for preparatory errors, such as aligning or crimping the valve in the wrong direction, or misuse of the various packaging components or assembly tools previously required for crimping the valves prior to implantation.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

What is claimed is:

1. A loader assembly for loading a transcatheter heart valve into a delivery sheath for delivering the heart valve into a body of a patient, the loader assembly comprising:
   a loader tube having a first end, a second end, and a central axis extending through the first and second ends, the loader tube comprising a tube wall defining a coaxial bore, wherein the tube wall has a first section at the first end with a first inner diameter, a second section connected to a distal end of the first section and having a second inner diameter smaller than the first inner diameter, and a third section connected to a distal end of the second section and having a third inner diameter greater than the second inner diameter;
   a hub in direct contact with and attached to at least an outer surface portion of the first section of the loader tube;
   a cap directly coupled to a proximal-most end of the hub; and
   at least one seal disposed in the cap and positioned proximal to the loader tube, the seal being configured to maintain hemostasis in the loader tube when the coaxial bore of the loader tube is in communication with a blood vessel of the patient;
   wherein the tube wall has a first tapered section between the first section and the second section, wherein the first tapered section has an inner surface that tapers in a direction extending from the first end towards the second end of the loader tube;
   wherein the tube wall has a second tapered section between the second section and the third section, wherein the second tapered section has an inner surface that tapers in a direction extending from the second end towards the first end of the loader tube, wherein the inner surface of the second tapered section progressively and continuously tapers from a proximal end of the third section to the distal end of the second section.

2. The loader assembly of claim 1, wherein the loader tube is separable into two or more separate parts.

3. The loader assembly of claim 2, wherein at least a portion of the first section of the loader tube has one or more score marks to facilitate separation of the loader tube into the two or more separate parts.

4. The loader assembly of claim 3, wherein the one or more score marks comprise two substantially parallel score marks extending from the first end of the loader tube to a transition region between the first section and the second section of the tube wall.

5. The loader assembly of claim 4, wherein the one or more score marks comprises a circumferential score mark extending circumferentially around the loader tube at the transition region between the first section and the second section of the tube wall.

6. The loader assembly of claim 1, wherein the third inner diameter is smaller than the first inner diameter.

7. The loader assembly of claim 1, wherein the hub comprises an annular lip that is configured to be threadably coupled to the cap.

8. The loader assembly of claim 1, wherein an axial length of the second section of the loader tube is longer than an axial length of the third section of the loader tube.

9. The assembly of claim 1, wherein the first section comprises a proximal cylindrical portion, a distal cylindrical portion, and a third tapered section extending from a distal end of the proximal cylindrical portion to a proximal end of the distal cylindrical portion.

10. The assembly of claim 9, wherein the inner surface of the first tapered section progressively and continuously tapers from the distal end of the first section to a proximal end of second section, and an inner surface of the third tapered section progressively and continuously tapers from the distal end of the proximal cylindrical portion to the proximal end of the distal cylindrical portion.

11. A loader assembly for loading a transcatheter heart valve into a delivery sheath for delivering the heart valve into a body of a patient, the loader assembly comprising:
    a loader tube having a first end, a second end, and a central axis extending through the first and second ends, the loader tube comprising a tube wall defining a coaxial bore, wherein the tube wall has a first section at the first end with a first diameter, a second section connected to a distal end of the first section and having a second diameter smaller than the first diameter, and a third section connected to a distal end of the second section and having a third diameter greater than the second diameter;
    a hub attached to at least a portion of the first section of the loader tube;
    a cap directly coupled to a proximal-most end of the hub; and
    at least one seal disposed in the cap and positioned proximal to the loader tube, the seal being configured to maintain hemostasis in the loader tube when the coaxial bore of the loader tube is in communication with a blood vessel of the patient;
    wherein the hub has a longitudinal slot, and wherein a portion of the loader tube is accessible through the slot to facilitate removal of the hub and the portion of the first section of the loader tube to which the hub is attached from other portions of the loader tube.

12. A loader assembly for loading a transcatheter heart valve into a delivery sheath for delivering the heart valve into a body of a patient, the loader assembly comprising:
    a loader tube having a first end, a second end, and a central axis extending through the first and second ends, the loader tube comprising a tube wall defining a coaxial bore, wherein the tube wall has a first section at the first end with a first diameter, a second section connected to a distal end of the first section and having a second diameter smaller than the first diameter, and a third section connected to a distal end of the second section and having a third diameter greater than the second diameter;
    a hub attached to at least a portion of the first section of the loader tube;

a cap directly coupled to a proximal-most end of the hub; and at least one seal disposed in the cap and positioned proximal to the loader tube, the seal being configured to maintain hemostasis in the loader tube when the coaxial bore of the loader tube is in communication with a blood vessel of the patient;

wherein the hub has an axial length that is substantially the same as an axial length of the first section of the loader tube.

13. The loader assembly of claim 12, wherein the first section of the loader tube comprises two axially extending score marks, the hub comprises a slot extending axially on one side of the hub, wherein a circumferential width of the slot is the same as or larger than a distance between the two score marks such that the two score marks are accessible through the slot.

14. An assembly for transcatheter implantation of an implantable device into a body of a patient, the assembly comprising:

a loader device comprising a loader tube, a first hub, a cap, and a first seal disposed in the cap; and a delivery sheath device comprising a second hub, a sheath attached to a distal end of the second hub, and a second seal disposed in the second hub;

wherein the loader tube having a first end, a second end, and a central axis extending through the first and second ends, the loader tube comprising a tube wall defining a coaxial bore, wherein the tube wall has a first section at the first end with a first diameter, a second section connected to a distal end of the first section and having a second diameter smaller than the first diameter, and a third section connected to a distal end of the second section and having a third diameter greater than the second diameter;

wherein the first hub is in direct contact with and attached to at least an outer surface portion of the first section of the loader tube and the cap is directly coupled to a proximal-most end of the first hub;

wherein the first hub has an axial length that is substantially the same as an axial length of the first section of the loader tube;

wherein the first seal is configured to maintain hemostasis in the loader tube when the coaxial bore of the loader tube is in communication with a blood vessel of the patient, and the second seal member is configured to maintain hemostasis when the sheath is in communication with the blood vessel of the patient; and wherein the second hub of the delivery sheath device is configured to receive at least the third section of the loader tube.

15. The assembly of claim 14, wherein the third section of the loader tube is configured to be advanced through the second seal and into the sheath.

16. The assembly of claim 14, wherein the sheath is expandable.

17. The assembly of claim 14, wherein the second section of the loader tube extends out of a proximal end of the second hub when a distal end of the third section of the loader tube is positioned at a distal end of the second hub.

18. The assembly of claim 14, further comprises a delivery catheter comprising a shaft and a balloon mounted on a distal end portion of the shaft, and a prosthetic valve radially crimped on or adjacent the balloon, wherein the balloon and the prosthetic valve are configured to be inserted distally through the first seal, the loader tube, the second seal, and into the sheath for introduction into the blood vessel of the patient.

19. The assembly of claim 18, wherein an axial length of the third section of the loader tube is equal to or greater than an axial length of the prosthetic valve.

20. The assembly of claim 19, wherein an axial length of the second section of the loader tube is greater than the axial length of the third section of the loader tube.

* * * * *